(12) United States Patent
Sakai et al.

(10) Patent No.: US 7,259,155 B2
(45) Date of Patent: Aug. 21, 2007

(54) PHOSPHONIC DIESTER DERIVATIVES

(75) Inventors: Yasuhiro Sakai, Nerima-ku (JP); Kazuyoshi Miyata, Itano-gun (JP); Takahiro Tomoyasu, Itano-gun (JP); Akiyoshi Kuroda, Saitama (JP); Yasuhide Inoue, Naruto (JP); Akifumi Hagi, Tokushima (JP); Shinya Miki, Itano-gun (JP); Norihiro Yoshinaga, Naruto (JP); Masako Doi, Naruto (JP); Yoshihiko Tsuda, Naruto (JP); Seiichirou Kanou, Sapporo (JP)

(73) Assignee: Otsuka Pharmaceutical Factory, Inc., Tokushima-ken (JP)

( * ) Notice: Subject to any disclaimer, the term of this patent is extended or adjusted under 35 U.S.C. 154(b) by 53 days.

(21) Appl. No.: 10/838,297

(22) Filed: May 5, 2004

(65) Prior Publication Data

US 2005/0256087 A1 Nov. 17, 2005

(51) Int. Cl.
*A61K 31/517* (2006.01)
*A61K 31/675* (2006.01)
*A01N 43/54* (2006.01)
*C07D 239/72* (2006.01)
*C07D 265/32* (2006.01)
*C07D 413/00* (2006.01)
*C07F 9/02* (2006.01)
*C07D 401/00* (2006.01)
*C07D 403/02* (2006.01)
*C07F 9/28* (2006.01)
*C07F 9/547* (2006.01)

(52) U.S. Cl. ............ 514/85; 514/266.2; 514/266.3; 514/266.4; 544/81; 544/87; 544/244; 544/287

(58) Field of Classification Search ............ 514/266.2, 514/266.3, 266.4, 81, 87, 85; 544/244, 287; 544/81, 87
See application file for complete search history.

(56) References Cited

U.S. PATENT DOCUMENTS 5,798,344 A * 8/1998 Kuroki et al. ............ 514/80

FOREIGN PATENT DOCUMENTS

JP 08-143586 6/1996

OTHER PUBLICATIONS

Inoue et al, "Antiatherogenic Effects of a Novel Selective Acyl-CoA: Cholesterol Acyltransferase-1 Inhibitor, OT-13398, in the Rat Carotid Artery with Experimental Altherosclerosis", 4th Annual Conference on Arteriosclerosis, Thrombosis and Vascular Biology, The American Heart Association, P74 (May 8-10, 2003).

* cited by examiner

*Primary Examiner*—Emily Berndhardt
*Assistant Examiner*—Tamthom N. Truong
(74) *Attorney, Agent, or Firm*—Sughrue Mion, PLLC

(57) ABSTRACT

The present invention provides a phosphonic acid diester compound represented by General Formula

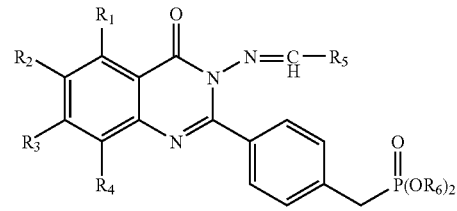

wherein $R_1$, $R_2$, $R_3$ and $R_4$ are the same or different, and represent hydrogen, halogen, lower alkyl or lower alkoxy; $R_5$ is phenyl having on the phenyl ring 1–3 substituents selected from the group consisting of lower alkyl, halogen-substituted lower alkyl, lower alkoxy, halogen-substituted lower alkoxy, phenoxy, benzyloxy, hydroxyl, halogen, nitro, lower alkylthio, di(lower alkyl)amino, lower alkanolyamino, pyrrolidinyl and phenyl, or the like, provided that $R_5$ is not mono(lower alkoxy)pheny; and $R_6$ is lower alkyl;

and an ACAT-1 inhibitor containing the compound as an active ingredient.

14 Claims, No Drawings

PHOSPHONIC DIESTER DERIVATIVES

BACKGROUND OF THE INVENTION

1. Field of the Invention

The present invention relates to novel phosphonic acid diester compounds and pharmaceuticals such as ACAT-1 (acyl-coenzyme A: cholesterol acyltransferase-1) inhibitors containing the same.

2. Description of the Related Art

Heretofore, compounds having ACAT inhibitory activity, i.e., ACAT inhibitors, are known such as urea derivatives having their structure derived from urea ($H_2N$—CO—$NH_2$), amide derivatives having amide (—NH—CO—) structure, imidazole derivatives having an imidazole ring, etc. (see, for example, Nihon Rinsho 59(suppliment 3), 2001, 675–680)

It is also known that compounds having ACAT inhibitory activity are effective as preventive and therapeutic agents for arteriosclerosis and as cholesterol absorption inhibitors (see, for example, The Journal of Biological Chemistry, Vol.276, No.28, July 14, pp.21324–21330, 2000 and The Journal of Biological Chemistry, Vol.275, No.36, September 8, pp.28083–28092, 2000 etc.).

Moreover, it has been recently reported that compounds having ACAT inhibitory activity are effective for treating Alzheimer's disease (see, for example, Mini. Rev. Med. Chem. 2003, September, 3(6): 576–584; Nat. Cell Biol., 2001, Octuber, 3(10), 905–912, etc.).

BRIEF SUMMARY OF THE INVENTION

An object of the present invention is to provide a novel compound having ACAT inhibitory activity and a pharmaceutical containing the same.

The inventors, during the process of researching and developing compounds for use as active ingredients in the pharmaceutical field, found that a series of novel compounds represented by General Formula (1) below have ACAT-1 inhibitory activity and are effective, for example, in the prevention and treatment of arteriosclerosis, and thereby accomplished the present invention.

The present invention provides phosphonic acid diester compounds represented by General Formula (1) below:

General Formula (1):

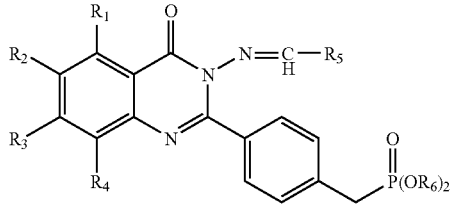

wherein $R_1$, $R_2$, $R_3$ and $R_4$ are the same or different, and represent hydrogen or halogen, or lower alkyl or lower alkoxy;

$R_5$ is phenyl having on the phenyl ring 1–3 substituents selected from the group consisting of lower alkyl, halogen-substituted lower alkyl, lower alkoxy, halogen-substituted lower alkoxy, phenoxy, benzyloxy, hydroxyl, halogen, nitro, lower alkylthio, di(lower alkyl)amino, lower alkanolyamino, pyrrolidinyl and phenyl, benzodioxolanyl,
naphthyl,
hydroxynaphthyl,
1-oxypyridyl,
pyridyl substituted with one lower alkyl,
thienyl optionally substituted with one member selected from the group consisting of lower alkyl, halogen and nitro,
furyl optionally substituted with one member selected from the group consisting of lower alkyl, halogen, nitro and halophenyl,
benzofuranyl,
pyrrolyl optionally substituted with one lower alkyl,
imidazolyl optionally substituted with one lower alkyl, or
indolyl, provided that $R_5$ is not mono(lower alkoxy) pheny; and
$R_6$ is lower alkyl.

In particular, the present invention provides (a) phosphonic acid diester compounds, wherein $R_5$ is imidazolyl optionally substituted with one lower alkyl, (b) phosphonic acid diester compounds, wherein $R_5$ is benzodioxolanyl, (c) phosphonic acid diester compounds, wherein $R_5$ is thienyl optionally substituted with one member selected from the group consisting of lower alkyl, halogen and nitro, or (d) phosphonic acid diester compounds, wherein $R_5$ is furyl optionally substituted with one member selected from the group consisting of lower alkyl, halogen, nitro and halophenyl.

The phosphonic acid diester compounds of the present invention are of use as arteriosclerosis preventive agents, arteriosclerosis therapeutic agents, LDL-cholesterol lowering agents, cholesterol absorption inhibitors, and Alzheimer's disease preventive and therapeutic agents.

Accordingly, the present invention provides a pharmaceutical composition for inhibiting ACAT-1, which comprises a phosphonic acid diester compound of General Formula (1) and a pharmaceutically acceptable carrier, and a method for providing an ACAT-1 inhibitory effect by administering to a patient in need of a treatment an effective amount of such a compound or such a composition.

DETAILED DESCRIPTION OF THE INVENTION

Groups used in General Formula (1) representing the compounds of the present invention and used elsewhere in this specification are as described below regardless of when they refer to skeletal groups in each formula or substituents in such groups. The term "lower" used herein in conjunction with groups containing carbon atoms is intended to mean "having 1 to 6 carbon atoms".

Examples of halogen atoms include fluorine, chlorine, bromine, iodine, etc.

Examples of lower alkyl groups include $C_{1-6}$ linear or branched alkyl groups such as methyl, ethyl, propyl, isopropyl, butyl, isobutyl, tert-butyl, pentyl, hexyl, etc.

Examples of lower alkoxy groups include $C_{1-6}$ linear or branched alkoxy groups such as methoxy, ethoxy, propoxy, isopropoxy, butoxy, isobutoxy, tert-butoxy, pentyloxy, hexyloxy, etc.

Examples of phenyl groups having on the phenyl ring 1–3 substituents selected from the group consisting of lower alkyl, halogen-substituted lower alkyl, lower alkoxy, halogen-substituted lower alkoxy, phenoxy, benzyloxy, hydroxyl, halogen, nitro, lower alkylthio, di(lower alkyl) amino, lower alkanolyamino, pyrrolidinyl and phenyl are:

phenyl groups substituted with lower alkyl, such as 2-methylphenyl, 3-methylphenyl, 4-methylphenyl, 4-ethylphenyl, 4-propylphenyl, 4-isopropylphenyl, 4-butylphenyl, 4-tert-butylphenyl, 4-pentylphenyl, 4-hexylphenyl and the like;

phenyl groups substituted with halogen-substituted lower alkyl, such as 2-trifluoromethylphenyl, 3-trifluoromethylphenyl, 4-trifluoromethylphenyl, 2-trichloromethylphenyl, 3-trichloromethylphenyl, 4-trichloromethylphenyl, 2-trichloromethylphenyl, 3-trichloromethylphenyl, 4-trichloromethylphenyl, 2-tribromomethylphenyl, 3-tribromomethylphenyl, 4-tribromomethylphenyl, 2-triiodomethylphenyl, 3-triiodomethylphenyl, 4-triiodomethylphenyl and the like;

phenyl groups substituted with lower alkoxy, such as 2-methoxyphenyl, 3-methoxyphenyl, 4-methoxyphenyl, 4-ethoxyphenyl, 4-propoxyphenyl, 4-isopropoxyphenyl, 4-butoxyphenyl, 4-isobutoxyphenyl, 4-tert-butoxyphenyl, 4-pentyloxyphenyl, 4-hexyloxyphenyl and the like;

phenyl groups substituted with halogen-substituted lower alkoxy, such as 2-trifluoromethoxyphenyl, 3-trifluoromethoxyphenyl, 4-trifluoromethoxyphenyl, 2-trichloromethoxyphenyl, 3-trichloromethoxyphenyl, 4-trichloromethoxyphenyl, 2-trichloromethoxyphenyl, 3-trichloromethoxyphenyl, 4-trichloromethoxyphenyl, 2-trichloromethoxyphenyl, 3-trichloromethoxyphenyl, 4-trichloromethoxyphenyl, 2-tribromomethoxyphenyl, 3-tribromomethoxyphenyl, 4-tribromomethoxyphenyl, 2-triiodomethoxyphenyl, 3-triiodomethoxyphenyl, 4-triiodomethoxyphenyl and the like;

phenoxyphenyl groups such as 2-phenoxyphenyl, 3-phenoxyphenyl, 4-phenoxyphenyl and the like;

benzylphenyl groups such as 2-benzylphenyl, 3-benzylphenyl, 4-benzylphenyl and the like;

phenyl groups substituted with hydroxyl, such as 2-hydroxyphenyl, 3-hydroxyphenyl, 4-hydroxyphenyl and the like;

phenyl groups substituted with halogen, such as 2-chlorophenyl, 3-chlorophenyl, 4-chlorophenyl, 2-fluorophenyl, 2-bromophenyl, 2-iodophenyl and the like;

phenyl groups substituted with nitro, such as 2-nitrophenyl, 3-nitrophenyl, 4-nitrophenyl and the like;

phenyl groups substituted with lower alkylthio, such as 2-methylthiophenyl, 3-methylthiophenyl, 4-methylthiophenyl, 4-ethylthiophenyl, 4-propylthiophenyl, 4-butylthiophenyl, 4-pentylthiophenyl, 4-hexylthiophenyl and the like;

phenyl groups having di(lower alkyl)amino, such as 2-dimethylaminophenyl, 3-dimethylaminophenyl, 4-dimethylaminophenyl, 4-diethylaminophenyl, 4-dipropylaminophenyl, 4-dibutylaminophenyl, 4-dipentylaminophenyl, 4-dihexylaminophenyl and the like;

phenyl groups having lower alkanolyamino, such as 2-acetylaminophenyl, 3-acetylaminophenyl, 4-acetylaminophenyl, 4-propanoylaminophenyl, 4-butanoylaminophenyl, 4-pentanoylaminophenyl, 4-hexanoylaminophenyl and the like;

phenyl groups having pyrrolidinyl, such as 2-pyrrolidinylphenyl, 3-pyrrolidinylphenyl, 4-pyrrolidinylphenyl and the like;

phenyl groups substituted with phenyl, such as 2-biphenyl, 3-biphenyl, 4-biphenyl and the like;

phenyl groups having 2 or 3 such substituents, such as 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 3,4,5-trimethoxyphenyl, 2,3,4-trimethoxyphenyl, 2,3-dichlorophenyl, 2,4-dichlorophenyl, 3,4-dichlorophenyl, 2-hydroxy-3-methoxyphenyl, 2-hydroxy-4-methoxyphenyl, 2-hydroxy-5-methoxyphenyl, 2-hydroxy-6-methoxyphenyl, 3-benzyloxy-4-methoxyphenyl and the like.

Examples of pyridyl groups substituted with one lower alkyl are those that have one $C_{1-6}$ alkyl, such as 3-methyl-2-pyridyl, 4-methyl-2-pyridyl, 5-methyl-2-pyridyl, 6-methyl-2-pyridyl, 2-methyl-3-pyridyl, 4-methyl-3-pyridyl, 5-methyl-3-pyridyl, 6-methyl-3-pyridyl, 2-methyl-4-pyridyl, 3-methyl-4-pyridyl and the like.

Examples of thienyl groups optionally substituted with one member selected from the group consisting of lower alkyl, halogen and nitro are 2-thienyl, 3-thienyl, 3-methyl-2-thienyl, 4-methyl-2-thienyl, 5-methyl-2-thienyl, 3-chloro-2-thienyl, 4-bromo-2-thienyl, 5-iodo-2-thienyl, 3-nitro-2-thienyl, 4-nitro-2-thienyl, 5-nitro-2-thienyl, 2-methyl-3-thienyl, 5-methyl-3-thienyl, 2-chloro-3-thienyl, 4-bromo-3-thienyl, 5-iodo-3-thienyl, 2-nitro-3-thienyl, 4-nitro-3-thienyl, 5-nitro-3-thienyl and the like.

Examples of furyl groups optionally substituted with one member selected from the group consisting of lower alkyl, halogen, nitro and halophenyl such as phenyl having 1 or 2 halogen atoms are 2-furyl, 3-furyl, 3-methyl-2-furyl, 4-methyl-2-furyl, 5-methyl-2-furyl, 3-chloro-2-furyl, 4-bromo-2-furyl, 5-iodo-2-furyl, 3-nitro-2-furyl, 4-nitro-2-furyl, 5-nitro-2-furyl, 2-methyl-3-furyl, 5-methyl-3-furyl, 2-chloro-3-furyl, 4-bromo-3-furyl, 5-iodo-3-furyl, 2-nitro-3-furyl, 4-nitro-3-furyl, 5-nitro-3-furyl, 3-(2-chlorophenyl)-2-furyl, 4-(3-chlorophenyl)-2-furyl, 5-(4-chlorophenyl)-2-furyl, 2-(4-chlorophenyl)-3-furyl, 4-(2-bromophenyl)-3-furyl, 5-(3-iodophenyl)-3-furyl and the like.

Examples of pyrrolyl groups optionally substituted with one lower alkyl are 2-pyrrolyl, 3-pyrrolyl, 1-methyl-2-pyrrolyl, 1-methyl-3-pyrrolyl, 1-ethyl-2-pyrrolyl, 1-ethyl-3-pyrrolyl, 1-propyl-2-pyrrolyl, 1-propyl-3-pyrrolyl and the like.

Examples of imidazolyl groups optionally substituted with one lower alkyl are 2-imidazolyl, 4(5)-imidazolyl, 4-methyl-5-imidazolyl and the like.

The compounds of the present invention represented by General Formula (1) have excellent ACAT-1 inhibitory action and are useful as ACAT-1 inhibitors. Taking advantage of such activity, these compounds are of use in the pharmaceutical field as arteriosclerosis preventive agents, arteriosclerosis therapeutic agents, LDL-cholesterol lowering agents, cholesterol absorption inhibitors, Alzheimer's disease preventive and therapeutic agents, etc.

Accordingly, the present invention provides pharmaceutical compositions for inhibiting ACAT-1 comprising compounds of the present invention represented by General Formula (1) and pharmaceutically acceptable carriers.

In particular, the present invention provides pharmaceutical compositions for treating arteriosclerosis comprising compounds of the present invention and pharmaceutically acceptable carriers; pharmaceutical compositions for inhibiting cholesterol absorption comprising compounds of the present invention and pharmaceutically acceptable carriers; pharmaceutical compositions for lowering LDL-cholesterol comprising compounds of the present invention and pharmaceutically acceptable carriers; and pharmaceutical compositions for treating Alzheimer's disease comprising compounds of the present invention and pharmaceutically acceptable carriers.

Furthermore, the present invention provides a method for inhibiting ACAT-1 in a patient in need such treatment, the method comprising administering to the patient an effective amount of a phosphonic acid diester compound represented by General Formula (1).

Moreover, the present invention provides a method for treating arteriosclerosis in a patient in need of such treatment, the method comprising administering to the patient an effective amount of a phosphonic acid diester compound represented by General Formula (1).

Further, the present invention provides a method for lowering the LDL-cholesterol level in a patient in need of such treatment, the method comprising administering to the patient an effective amount of a phosphonic acid diester compound represented by General Formula (1).

In addition, the present invention provides a method for inhibiting the cholesterol absorption in a patient in need of such treatment, the method comprising administering to the patient an effective amount of a phosphonic acid diester compound represented by General Formula (1).

Furthermore, the present invention provides a method for treating Alzheimer's disease in a patient in need of such treatment, the method comprising administering to the patient an effective amount of a phosphonic acid diester compound represented by General Formula (1).

Compounds of the present invention preferable in the pharmaceutical field are (a) phosphonic acid diester compounds represented by General Formula (1) wherein $R_3$ is halogen. Such compounds have the advantage of maintaining a high concentration in the blood especially when administered orally. Among Compounds (a), (b) phosphonic acid diester compounds wherein $R_5$ is thienyl optionally substituted with one member selected from the group consisting of lower alkyl, halogen and nitro; (c) phosphonic acid diester compounds wherein $R_5$ is imidazolyl optionally substituted with one lower alkyl; and (d) phosphonic acid diester compounds wherein $R_5$ is benzodioxolanyl exhibit stronger ACAT-1 inhibitory activity in that order. Therefore, the phosphonic acid diester compounds (d) can be given as examples that have the strongest ACAT-1 inhibitory activity.

Among the compounds of the present invention, particularly preferable for medical purposes are compounds categorized into the following 2 groups (Group A and Group B):

Group A: phosphonic acid diester compounds represented by General Formula (1) wherein $R_1$, $R_2$ and $R_4$ are hydrogen;

$R_3$ is halogen, and chlorine in particular;

$R_5$ is imidazolyl; and $R_6$ is lower alkyl, and ethyl in particular.

Group B: phosphonic acid diester compounds represented by General Formula (1) wherein $R_1$, $R_2$ and $R_4$ are hydrogen;

$R_3$ is halogen, and chlorine in particular;

$R_5$ is benzodioxolanyl; and $R_6$ is lower alkyl, and ethyl in particular.

The most preferable example of the compounds of the present invention belonging to Group A above is diethyl (4-{7-chloro-3-[(1H-imidazol-2-ylmethylene)amino]-4-oxo-3,4-dihydroquinazolin-2-yl}benzylphosphonate. The most preferable example of the compounds of the present invention belonging to Group B above is diethyl (4-{3-[(benzo[1,3]dioxol-5-ylmethylene)amino]-7-chloro-4-oxo-3,4-dihydroquinazolin-2-yl}benzylphosphonate.

A method for preparing the compounds of the present invention is described below.

The compounds of the present invention can be prepared according to, for example, Reaction Scheme 1 given below:

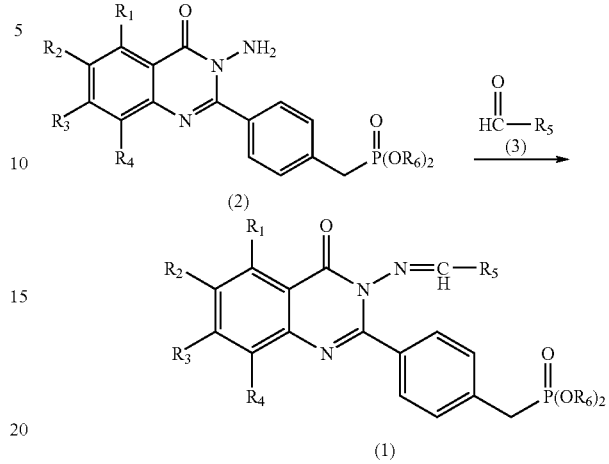

wherein $R_1$, $R_2$, $R_3$, $R_4$, $R_5$ and $R_6$ are the same as in General Formula (1).

According to Reaction Scheme 1, a compound of the present invention (1) can be obtained by reacting a known compound (2) with a known aldehyde (3).

The above reaction can be conducted using about equimolar to about 1.2-fold molar amount of aldehyde (3) in the presence of a catalytic amount of an acid catalyst such as concentrated hydrochloric acid, concentrated sulfuric acid, p-toluenesulfonic acid or the like either in the absence of a solvent or in the presence of a suitable inert solvent such as N,N-dimethylformamide (DMF), tetrahydrofuran (THF) or 1,4-dioxane. The reaction temperature is room temperature to about the reflux temperature of the solvent. The reaction usually completes in about 2 to about 30 hours.

Compound (2) used as a starting material in the reaction illustrated by Reaction Scheme 1 can be prepared according to the method disclosed in Japanese Unexamined Patent Publication No. 143586/1996. This publication is incorporated herein by reference. This publication discloses a compound similar to the phosphonic acid diester compounds of the present invention in which —N═CHR$_5$ in General Formula (1) is benzylideneamino optionally substituted with lower alkoxy on the phenyl ring. This publication discloses that this compound is effective as agents for treating hyperlipidemia, hypertension and diabetes mellitus. However, this publication does not disclose that this compound has an ACAT inhibitory activity. Furthermore, this publication neither discloses nor suggests that this compound is effective as an arteriosclerosis preventive and therapeutic agent, cholesterol absorption inhibitor and Alzheimer's disease preventive and therapeutic agent due to the ACAT inhibitory activity.

The compounds of the present invention can be readily isolated and purified according to conventional separation and purification methods. Such methods include generally used techniques such as adsorption chromatography, preparative thin-layer chromatography, recrystallization, solvent extraction, etc.

The present invention also provides a pharmaceutical composition containing a compound of the present invention represented by General Formula (1) as an active ingredient. Such a pharmaceutical composition is prepared by formulating a compound of the present invention and a pharmaceutically acceptable carrier into a conventional pharmaceutical preparations, and put into practical use.

Examples of pharmaceutically acceptable carriers for use in the pharmaceutical composition of the present invention include fillers, extenders, binders, humectants, disintegrants, surfactants, lubricants, and like diluents and excipients that are usually used depending on the application of the pharmaceutical preparations. These carriers are suitably selected according to the unit dosage form of the pharmaceutical preparations to be created.

A variety of unit dosage forms can be suitably selected for the pharmaceutical compositions according to their therapeutic purposes. Typical examples are tablets, pills, powders, solutions, suspensions, emulsions, granules, capsules, suppositories, injections (solutions, suspensions, etc.), ointments, etc.

In producing tablets, pharmaceutically acceptable carriers include lactose, saccharose, sodium chloride, glucose, urea, starch, calcium carbonate, kaolin, crystalline cellulose, silicic acid, potassium phosphate, and like excipients; water, ethanol, propanol, simple syrup, glucose solution, starch solution, gelatin solution, carboxylmethylcellulose, hydroxypropylcellulose, methyl-cellulose, polyvinylpyrrolidone, and like binders; sodium carboxymethylcellulose, calcium carboxymethylcellulose, low-substituted hydroxypropylcellulose, dried starch, sodium alginate, powdered agar, powdered laminaran, sodium hydrogencarbonate, calcium carbonate, and like disintegrants; polyoxyethylene sorbitan fatty acid esters, sodium lauryl sulfate, stearic acid monoglyceride, and like surfactants; saccharose, stearin, cacao butter, hydrogenated oils, and like disintegration inhibitors; quaternary ammonium bases, sodium lauryl sulfate, and like absorption enhancers; glycerin, starch, and like humectants; starch, lactose, kaolin, bentonite, colloidal silica, and like absorbents; purified talc, stearate, boric acid powder, polyethylene glycol, and like lubricants; etc. Furthermore, tablets can be formulated with conventional coatings if necessary, for example, sugar-coated, gelatin-coated, enteric-coated, or film-coated, double- or multi-layer tablets, etc.

In producing pills, pharmaceutically acceptable carriers include, for example, glucose, lactose, starch, cacao butter, hydrogenated vegetable oil, kaolin, talc, and like excipients; powdered gum arabic, powdered tragacanth, gelatin, ethanol, and like binders; laminaran, agar, and like disintegrants; etc.

In producing suppositories, pharmaceutically acceptable carriers include, for example, polyethylene glycol, cacao butter, higher alcohols and their esters, gelatin, semisynthetic glycerides, etc.

Capsules can be prepared in a conventional manner usually by encapsulating compounds of the present invention in combination with the aforementioned pharmaceutically acceptable carriers into hard gelatin capsules, soft gelatin capsules, and the like.

When the pharmaceutical compositions of the invention are formulated into injectable forms such as solutions, emulsions, suspensions, and the like, they are preferably sterilized and made isotonic to blood. In formulating into injections, examples of diluents usable are water, ethanol, macrogol, propyleneglycol, ethoxylated isostearyl alcohol, polyoxylated isostearyl alcohol, polyoxyethylene sorbitan fatty acid esters, etc. Common salt, glucose, or glycerin can be used in the pharmaceutical preparations in an amount sufficient to produce isotonic solutions. Furthermore, conventional auxiliary cosolvents, buffers, soothing agents can be added to the solutions.

When the pharmaceutical compositions of the invention are formulated into ointments, such as paste, cream, gel, and the like, examples of diluents usable are white petrolatum, paraffin, glycerin, cellulose compounds, polyethylene glycol, silicone, bentonite, etc.

Moreover, as necessary, colorants, preservatives, aroma chemicals, flavorings, sweeteners, etc., and other pharmaceuticals can be used in the pharmaceutical compositions of the invention.

The amount of compound of the present invention (active compound) contained in the pharmaceutical composition of the present invention is not limited and can be suitably selected from a wide range. It is generally preferable that the active compound accounts for about 0.5 to about 90 wt. %, preferably about 1 to about 85 wt. %, of the pharmaceutical composition.

Administration routes for the pharmaceutical preparations of the present invention are not limited, and can be selected according to the form of each preparation, age, gender and other conditions of the patient, and severity of the disease. For example, tablets, pills, solutions, suspensions, emulsions, granules, and capsules are administered orally. Injections are intravenously, intramuscularly, intracutaneously, subcutaneously, or intraperitoneally administered alone or in combination with glucose, amino acid, or like conventional replenisher fluids. Suppositories are administered intrarectally.

Dosage of the pharmaceutical preparation of the invention can be suitably selected according to the application, age, gender and other conditions of the patient, and degree of the disease. Usually, the pharmaceutical preparation is administered such that the active ingredient, i.e., the compound of the present invention, is given to a human adult in a dose of about 0.5 to about 20 mg, and preferably about 1 to about 10 mg, per kg body weight. The pharmaceutical preparation can be given in a single dose or divided (2 to 4) doses per day.

EXAMPLES

To illustrate the invention in more detail, production examples of the compounds of the present invention, pharmacological test examples conducted with respect to the compounds, and formulation examples of pharmaceuticals containing a compound of the present invention as an active ingredient are given below.

In the examples, unless otherwise specified, $^1$H-NMR spectroscopy was conducted in chloroform-$d_1$(CDCl$_3$) solvent, using tetramethylsilane (TMS) as an internal standard.

Example 1

Preparation of diethyl 4-(7-chloro-3-N-(4-methylbenzylideneamin)-4(3H)-quinazolinon-2-yl)benzylphosphonate (Compound 1)

Diethyl 4-(3-amino-7-chloro-4(3H)-quinazolinon-2-yl) benzylphosphonate (0.5 g), p-tolualdehyde (0.28 ml) and a catalytic amount of p-toluenesulfonic acid were suspended in N,N-dimethylformamide (5 ml) and stirred for 2 hours at room temperature. After reaction, ice-cooled water was introduced into the reaction solution, and the thus-produced precipitate was filtered off. The thus-obtained crude product was recrystallized from chloroform/diethyl ether, thereby giving 0.51 g of a white powder of the desired product.

Table 1 shows the structure and properties of the compound obtained above.

Examples 2–152

The compounds shown in Tables 1–31 (Examples 2–152) were prepared in the same manner as in Example 1 except that the p-tolualdehyde was replaced with various suitable aldehydes. Tables 1–31 also show the structure ($R_1$, $R_2$, $R_3$, $R_4$ and $R_5$ in General Formula (1) are identified, and each $R_6$ is ethyl) and properties of each compound thereby obtained.

In the tables, the abbreviations used to indicate the groups are:

Me: methyl, Et: ethyl, Ph: phenyl, Bn: benzyl, Me$_2$: dimethyl, Ac: acetyl, OMe or MeO: methoxy, OBn: benzyloxy, SMe: methylthio.

TABLE 1

| Ex. | R₁ | R₂ | R₃ | R₄ | R₅ | ¹H-NMR (δ: ppm) [CDCl₃] |
|---|---|---|---|---|---|---|
| 1 | H | H | Cl | H | 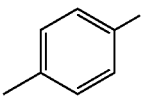 | 8.90 (s, 1 H), 8.29 (d, J=8.7 Hz, 1 H), 7.80 (d, J=2.1 Hz, 1 H), 7.69 (d, J=7.9 Hz, 2 H), 7.59 (d, J=8.3 Hz, 2 H), 7.47 (dd, J=2.1, 8.3 Hz, 1 H), 7.36 (dd, J=2.5, 8.3 Hz, 2 H), 7.22 (d, J=8.3 Hz, 2 H), 4.07–.395 (m, 4 H), 3.19 (d, J=22.0 Hz, 2 H), 2.40 (s, 3 H), 1.22 (t, J=7.1 Hz, 6 H). |
| 2 | H | H | Cl | H | 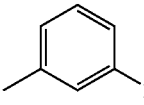 | 8.91 (s, 1 H), 8.27 (d, J=8.7 Hz, 1 H), 7.80 (d, J=2.1 Hz, 1 H), 7.70 (d, J=7.9 Hz, 2 H), 7.52–7.45 (m, 3 H), 7.37 (dd, J=2.5, 8.3 Hz, 2 H), 7.33–7.28 (m, 2 H), 4.07–3.94 (m, 4 H), 3.19 (d, J=22.0 Hz, 2 H), 2.37 (s, 3 H), 1.21 (t, J=7.1 Hz, 6 H). |
| 3 | H | H | Cl | H | 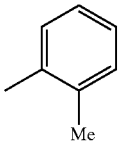 | 9.22 (s, 1 H), 8.29 (d, J=8.7 Hz, 1 H), 7.81 (d, J=1.7 Hz, 1 H), 7.70 (d, J=2.9 Hz, 1 H), 7.70–7.67m (m, 3 H), 7.48 (dd, J=2.1, 8.3 Hz, 1 H), 7.40–7.35 (m, 2 H), 7.24–7.18 (m, 2 H), 4.06–3.97 (m, 4 H), 3.20 (d, J=22.0 Hz, 2 H), 2.47 (s, 3 H), 1.23 (t, J=7.1 Hz, 6 H). |
| 4 | H | H | Cl | H | 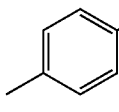 | 8.91 (s, 1 H), 8.28 (d, J=8.3 Hz, 1 H), 7.80 (d, J=1.7 Hz, 1 H), 7.70 (d, J=7.9 Hz, 2 H), 7.62 (d, J=8.3 Hz, 2 H), 7.47 (dd, J=2.1, 8.7 Hz, 1 H), 7.37 (dd, J=2.5, 8.3 Hz, 2 H), 7.24 (d, J=7.9 Hz, 2 H), 4.05–3.95 (m, 4 H), 3.19 (d, J=22.0 Hz, 2 H), 2.69 (q, J=7.5 Hz, 2 H), 1.25 (t, J=7.5 Hz, 3 H), 1.22 (t, J=7.1 Hz, 6 H). |
| 5 | H | H | Cl | H | 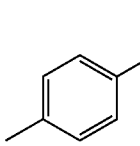 | 8.91 (s, 1 H), 8.27 (d, J=8.7 Hz, 1 H), 7.80 (d, J=2.1 Hz, 1 H), 7.70 (d, J=7.5 Hz, 2 H), 7.63 (d, J=8.3 Hz, 2 H), 7.47 (dd, J=2.1, 8.7 Hz, 1 H), 7.37 (dd, J=2.5, 8.3 Hz, 2 H), 7.28–7.26 (m, 2 H), 4.05–3.95 (m, 4 H), 3.20 (d, J=22.0 Hz, 2 H), 2.94 (septet, J=7.1 Hz, 1 H), 1.29 (d, J=7.1 Hz, 6 H), 1.21 (t, J=7.1 Hz, 6 H). |

TABLE 2

| Ex. | R₁ | R₂ | R₃ | R₄ | R₅ | ¹H-NMR (δ: ppm) [CDCl₃] |
|---|---|---|---|---|---|---|
| 6 | H | H | Cl | H | 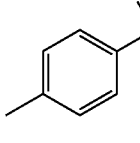 | 8.92 (s, 1 H), 8.29 (d, J=8.7 Hz, 1 H), 7.80 (d, J=2.1 Hz, 1 H), 7.70 (d, J=8.3 Hz, 2 H), 7.64 (d, J=8.3 Hz, 2 H), 7.48–7.43 (m, 3 H), 7.37 (dd, J=2.1, 8.3 Hz, 2 H), 4.04–3.96 (m, 4 H), 3.20 (d, J=21.6 Hz, 2 H), 1.33 (s, 9 H), 1.22 (t, J=7.1 Hz, 6 H). |
| 7 | H | H | Cl | H | 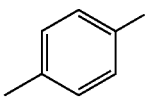 | 9.24 (s, 1 H), 8.28 (d, J=8.7 Hz, 1 H), 7.81 (d, J=2.1 Hz, 1 H), 7.79 (d, J=8.3 Hz, 2 H), 7.67 (d, J=8.3 Hz, 4 H), 7.49 (dd, J=2.1, 8.7 Hz, 1 H), 7.39 (dd, J=2.5, 8.3 Hz, 2 H), 4.07–3.99 (m, 4 H), 3.21 (d, J=22.0 Hz, 2 H), 1.23 (t, J=7.1 Hz, 6 H). |

TABLE 2-continued

| Ex. | R₁ | R₂ | R₃ | R₄ | R₅ | ¹H-NMR (δ: ppm) [CDCl₃] |
|---|---|---|---|---|---|---|
| 8 | H | H | Cl | H | 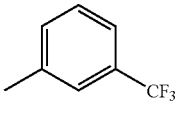 | 9.20 (s, 1 H), 8.28 (d, J=8.7 Hz, 1 H), 7.94 (s, 1 H), 7.86 (d, J = 7.5 Hz, 1 H), 7.81 (d, J=2.1 Hz, 1 H), 7.75 (d, J=7.9 Hz, 1 H), 7.68 (d, J=7.5 Hz, 2 H), 7.56 (t, J= 7.9 Hz, 1 H), 7.49 (dd, J=2.1, 8.3 Hz, 1 H), 7.39 (dd, J=2.5, 8.3 Hz, 2 H), 4.06–3.99 (m, 4 H), 3.21 (d, J=22.0 Hz, 2 H), 1.23 (t, J=7.1 Hz, 6 H). |
| 9 | H | H | Cl | H | 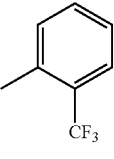 | 9.51 (d, J=1.7 Hz, 1 H), 8.31 (d, J=8.3 Hz, 1 H), 7.98 (d, J=7.5 Hz, 1 H), 7.81 (d, J=2.1 Hz, 1 H), 7.75 (d, J=7.5 Hz, 1 H), 7.64 (d, J=7.5 Hz, 2 H), 7.61–7.54 (m, 2 H), 7.49 (dd, J=2.1, 8.7 Hz, 1 H), 7.38 (dd, J=2.5, 8.3 Hz, 2 H), 4.06–3.96 (m, 4 H), 3.20 (d, J=22.0 Hz, 2 H), 1.21 (t, J=7.1 Hz, 6 H). |
| 10 | H | H | Cl | H | 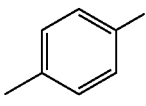 | 9.09 (s, 1 H), 8.27 (d, J=8.7 Hz, 1 H), 7.81 (d, J=2.1 Hz, 11 H), 7.73 (d, J=8.7 Hz, 2 H), 7.67 (d, J= 7.5 Hz, 2 H), 7.48 (dd, J=2.1, 8.3 Hz, 1 H), 7.39 (dd, J=2.1, 8.3 Hz, 2 H), 7.29–7.25 (m, 2 H), 4.07–3.98 (m, 4 H), 3.20 (d, J=22.0 Hz, 2 H), 1.23 (t, J=7.1 Hz, 6 H). |

TABLE 3

| Ex. | R₁ | R₂ | R₃ | R₄ | R₅ | ¹H-NMR (δ: ppm) [CDCl₃] |
|---|---|---|---|---|---|---|
| 11 | H | H | Cl | H | 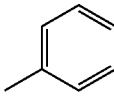 | 9.15(s, 1H), 8.28(d, J=8.7Hz, 1H), 7.81(d, J=1.7Hz, 1H), 7.68 (d, J=7.9Hz, 2H), 7.60(d, J= 7.9Hz, 1H), 7.54(s, 1H), 7.50–7.33 (m, 5H), 4.07–3.96(m, 4H), 3.21 (d, J=22.0Hz, 2H), 1.23(t, J= 7.1Hz, 6H). |
| 12 | H | H | Cl | H | 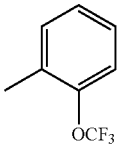 | 9.36(s, 1H), 8.30(d, J=8.3Hz, 1H), 7.88(dd, J=1.7, 7.9Hz, 1 H), 7.80(d, J=2.1Hz, 1H), 7.65 (d, J=7.5Hz, 2H), 7.54(ddd, J= 1.7, 7.5, 8.3Hz, 1H), 7.49(dd, J=2.1, 8.7Hz, 1H), 7.39–7.28(m, 4H), 4.05–3.96(m, 4H), 3.19(d, J=22.0Hz, 2H), 1.20(t, J=7.1 Hz, 6H). |
| 13 | H | H | Cl | H | 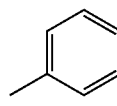 | 8.90(s, 1H), 8.27(d, J=8.3Hz, 1H), 7.80(d, J=2.1Hz, 1H), 7.70–7.64(m, 4H), 7.47(dd, J= 2.1, 8.7Hz, 1H), 7.42–7.36(m, 4 7.07–7.05(m, 2H), 6.98(d, J=8.7 Hz, 2H), 4.05–3.96(m, 4H), 3.19 (d, J=21.6Hz, 2H), 1.22(t, J= 7.1Hz, 6H). |
| 14 | H | H | Cl | H | 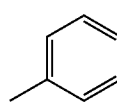 | 8.96(s, 1H), 8.26(d, J=8.7Hz, 1H), 7.79(d, J=2.1Hz, 1H), 7.67 (d, J=7.9Hz, 2H), 7.47(dd, J= 2.1, 8.7Hz, 1H), 7.42–7.33(m, 7H), 7.17–7.12(m, 2H), 7.01(dd, J=1.2, 8.7Hz, 2H), 4.05–3.97(m, 4H), 3.19(d, J=22.0Hz, 2H), 1.22(t, J=7.1Hz, 6H). |

TABLE 3-continued

| Ex. | R₁ | R₂ | R₃ | R₄ | R₅ | ¹H-NMR (δ: ppm) [CDCl₃] |
|---|---|---|---|---|---|---|
| 15 | H | H | Cl | H | 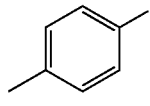 | 8.81(s, 1H), 8.27(d, J=8.3Hz, 1H), 7.80(d, J=1.7Hz, 1H), 7.69 (d, J=7.9Hz, 2H), 7.65(d, J= 9.1Hz, 2H), 7.46(dd, J=2.1, 8.7 Hz, 1H), 7.43–7.33(m, 7H), 6.99 (d, J=8.7Hz, 2H), 5.12(s, 2H), 4.04–3.96(m, 4H), 3.19(d, J=22.0 Hz, 2H), 1.21(t, J=7.1Hz, 6H). |

TABLE 4

| Ex. | R₁ | R₂ | R₃ | R₄ | R₅ | ¹H-NMR (δ: ppm) [CDCl₃] |
|---|---|---|---|---|---|---|
| 16 | H | H | Cl | H | 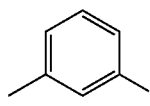 | 8.96 (s, 1 H), 8.28 (d, J=8.3 Hz, 1 H), 7.80 (d, J=2.1 Hz, 1 H), 7.69 (d, J=7.5 Hz, 2 H), 7.47 (dd, J= 2.1, 8.7 Hz, 1 H), 7.43–7.28 (m, 10 H), 7.11 (ddd, J=1.2, 2.5, 7.9 Hz, 1 H), 5.04 (s, 2 H), 4.03–3.95 (m, 4 H), 3.17 (d, J=22.0 Hz, 2 H), 1.20 (t, J=7.1 Hz, 6 H). |
| 17 | H | H | Cl | H | 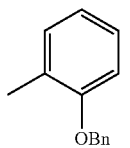 | 9.30 (s, 1 H), 8.28 (d, J=8.3 Hz, 1 H), 7.85 (dd, J=1.7, 7.9 Hz, 1 H), 7.79 (d, J=1.7 Hz, 1 H), 7.69 (d, J=7.5 Hz, 2 H), 7.47–7.31 (m, 9 H), 6.98 (d, J=8.3 Hz, 1 H), 6.94 (t, J=7.5 Hz, 1 H), 5.15 (s, 2 H), 4.04–3.94 (m, 4 H), 3.18 (d, J=21.6 Hz, 2 H), 1.20 (t, J=7.1 Hz, 6 H). |
| 18 | H | H | Cl | H | 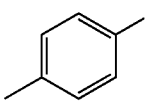 | 8.65 (s, 1 H), 8.24 (d, J=8.7 Hz, 1 H), 7.17 (brs, 1 H), 7.80 (d, J= 2.1 Hz, 1 H), 7.67 (d, J=7.9 Hz, 2 H), 7.52–7.44 (m, 3 H), 7.35 (dd, J=2.5, 8.3 Hz, 2 H), 6.75 (d, J= 8.3 Hz, 2 H), 4.04–3.93 (m, 4 H), 3.20 (d, J=22.0 Hz, 2 H), 1.21 (t, J=7.1 Hz, 6 H). |
| 19 | H | H | Cl | H | 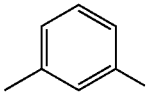 | 9.57 (s, 1 H), 9.15 (s, 1 H), 8.30 (d, J=8.7 Hz, 1 H), 7.81 (d, J= 1.7 Hz, 1 H), 7.55 (d, J=7.9 Hz, 2 H), 7.50 (dd, J=2.1, 8.7 Hz, 1 H), 7.41 (dd, J=2.5, 8.3 Hz, 2 H), 7.29–7.25 (m, 1 H), 7.03 (d, J=7.5 Hz, 1 H), 6.95 (dd, J=2.1, 8.3 Hz, 1 H), 6.70 (S. 1 H), 4.10–4.03 (m, 4 H), 3.26 (d, J=22.0 Hz, 2 H), 1.29 (t, J=7.1 Hz, 6 H). |
| 20 | H | H | Cl | H | 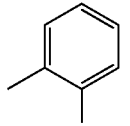 | 10.02 (s, 1 H), 9.09 (s, 1 H), 8.28 (d, J=8.7 Hz, 1 H), 7.81 (d, J= 2.1 Hz, 1 H), 7.59 (d, J=7.9 Hz, 2 H), 7.50 (dd, J=2.1, 8.7 Hz, 1 H), 7.43–7.34 (m, 4 H), 6.96 (t, J= 7.5 Hz, 1 H), 6.88 (d, J=8.3 Hz, 1 H), 4.05–3.97 (m, 4 H), 3.21 (d, Hz, 6 H). |

TABLE 5

| Ex. | R₁ | R₂ | R₃ | R₄ | R₅ | ¹H-NMR (δ: ppm) [CDCl₃] |
|---|---|---|---|---|---|---|
| 21 | H | H | Cl | H | 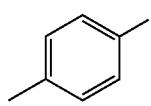 | 9.04 (s, 1 H), 8.27 (d, J=8.3 Hz, 1 H), 7.80 (d, J=1.7 Hz, 1 H), 7.67 (d, J=7.9 Hz, 2 H), 7.62 (d, J= 8.3 Hz, 2 H), 7.48 (dd, J=1.7, 8.3 Hz, 1 H), 7.40–7.36 (m, 4 H), 4.07–3.96 (m, 4 H), 3.20 (d, J=22.0 Hz, 2 H), 1.22 (t, J=7.1 Hz, 6 H). |

TABLE 5-continued

| Ex. | R₁ | R₂ | R₃ | R₄ | R₅ | ¹H-NMR (δ: ppm) [CDCl₃] |
|---|---|---|---|---|---|---|
| 22 | H | H | Cl | H | 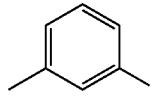 | 9.05 (s, 1 H), 8.27 (d, J=8.7 Hz, 1 H), 7.81 (d, J=2.1 Hz, 1 H), 7.69–7.67 (m, 3 H), 7.55 (d, J=7.9 Hz, 1 H), 7.49–7.45 (m, 2 H), 7.41–7.34 (m, 3 H), 4.07–3.98 (m, 4 H), 3.21 (d, J=22.0 Hz, 2 H), 1.23 (t, J=7.1 Hz, 6 H). |
| 23 | H | H | Cl | H | 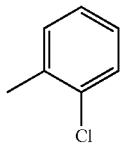 | 9.51 (s, 1 H), 8.30 (d, J=8.3 Hz, 1 H), 7.83–7.80 (m, 2 H), 7.67 (d, J=7.9 Hz, 2 H), 7.48 (dd, 2.1, 8.7 Hz, 1 H), 7.46–7.37 (m, 4 H), 7.29–7.23 (m, 1 H), 4.08–3.95 (m, 4 H), 3.20 (d, J=22.0 Hz, 2 H), 1.22 (t, J=7.1 Hz, 6 H). |
| 24 | H | H | Cl | H | 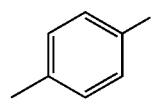 | 8.99 (s, 1 H), 8.27 (d, J=8.7 Hz, 1 H), 7.80 (d, J=1.7 Hz, 1 H), 7.72–7.67 (m, 4 H), 7.48 (dd, J=2.1, 8.7 Hz, 1 H), 7.38 (dd, J=2.5, 8.3 Hz, 2 H), 7.13–7.08 (m, 2 H), 4.08–3.97 (m, 4 H), 3.20 (d, J=22.0 Hz, 2 H), 1.23 (t, J=7.1 Hz, 6 H). |
| 25 | H | H | Cl | H | 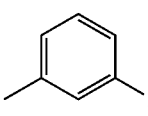 | 9.10 (d, J=0.8 Hz, 1 H), 8.28 (d, J=8.3 Hz, 1 H), 7.81 (d, J=2.1 Hz, 1 H), 7.68 (d, J=7.5 Hz, 2 H), 7.48 (dd, J=2.1, 8.7 Hz, 1 H), 7.45–7.34 (m, 6 H), 7.22–7.17 (m, 1 H), 4.07–3.98 (m, 4 H), 3.21 (d, J=22.0 Hz, 2 H), 1.23 (t, J=7.1 Hz, 6 H). |
| 26 | H | H | Cl | H | 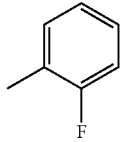 | 9.30 (s, 1 H), 8.29 (d, J=8.3 Hz, 1 H), 7.82–7.78 (m, 2 H), 7.68 (d, J=7.9 Hz, 2 H), 7.52–7.46 (m, 2 H), 7.38 (dd, J=2.5, 8.4 Hz, 2 H), 7.17–7.12 (m, 2 H), 4.08–3.96 (m, 4 H), 3.20 (d, J=22.0 Hz, 2 H), 1.22 (t, J=7.1 Hz, 6 H). |

TABLE 6

| Ex. | R₁ | R₂ | R₃ | R₄ | R₅ | ¹H-NMR (δ: ppm) [CDCl₃] |
|---|---|---|---|---|---|---|
| 27 | H | H | Cl | H | 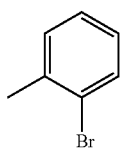 | 9.49 (s, 1 H), 8.31 (d, J=8.7 Hz, 1 H), 7.81–7.79 (m, 2 H), 7.67 (d, J=7.9 Hz, 2 H), 7.63 (d, J=7.5 Hz, 1 H), 7.48 (dd, J=2.1, 8.7 Hz, 1 H), 7.39 (dd, J=2.1, 8.3 Hz, 2 H), 7.36–7.29 (m, 2 H), 4.05–3.98 (m, 4 H), 3.20 (d, J=22.0 Hz, 2 H), 1.22 (t, J=7.1 Hz, 6 H). |
| 28 | H | H | Cl | H | 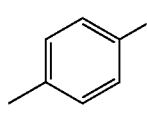 | 9.42 (s, 1 H), 8.29–8.25 (m, 3 H), 7.84–7.80 (m, 3 H), 7.66 (d, J=7.9 Hz, 2 H), 7.50 (dd, J=2.1, 8.7 Hz, 1 H), 7.40 (dd, J=2.5, 8.3 Hz, 2 H), 4.10–4.01 (m, 4 H), 3.22 (d, J=22.0 Hz, 2 H), 1.25 (t, J=7.1 Hz, 6 H). |
| 29 | H | H | Cl | H | 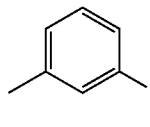 | 9.36 (s, 1 H), 8.51–8.50 (m, 1 H), 8.35–8.33 (m, 1 H), 8.28 (d, J=8.3 Hz, 1 H), 7.98 (d, J=7.9 Hz, 1 H), 7.82 (d, J=1.7 Hz, 1 H), 7.68 (d, J=8.3 Hz, 2 H), 7.62 (t, J=7.9 Hz, 1 H), 7.50 (dd, J=2.1, 8.7 Hz, 1 H), 7.41 (dd, J=2.1, 8.3 Hz, 2 H), 4.07–4.00 (m, 4 H), 3.22 (d, J=22.0 Hz, 2 H), 1.24 (t, J=7.1 Hz, 6 H). |

TABLE 6-continued

| Ex. | R₁ | R₂ | R₃ | R₄ | R₅ | ¹H-NMR (δ: ppm) [CDCl₃] |
|---|---|---|---|---|---|---|
| 30 | H | H | Cl | H | 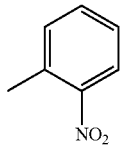 | 9.59 (s, 1 H), 8.29 (d, J=8.3 Hz, 1 H), 8.17–8.15 (m, 1 H), 7.91–7.89 (m, 1 H), 7.82 (d, J=2.1 Hz, 1 H), 7.70–7.65 (m, 4 H), 7.49 (dd, J=2.1, 8.7 Hz, 1 H), 7.37 (dd, J=2.5, 8.3 Hz, 2 H), 4.04–3.96 (m, 4 H), 3.18 (d, J=22.0 Hz, 2 H), 1.20 (t, J=7.1 Hz, 6 H). |
| 31 | H | H | Cl | H | 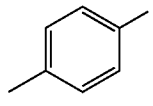 | 8.90 (s, 1 H), 8.27 (d, J=8.7 Hz, 1 H), 7.80 (d, J=1.7 Hz, 1 H), 7.69 (d, J=7.9 Hz, 2 H), 7.59 (d, J=8.7 Hz, 2 H), 7.47 (dd, J=2.1, 8.7 Hz, 1 H), 7.37 (dd, J=2.1, 8.3 Hz, 2 H), 7.23 (d, J=8.7 Hz, 2 H), 4.05–3.97 (m, 4 H), 3.19 (d, J=22.0 Hz, 2 H), 2.51 (s, 3 H), 1.22 (t, J=7.1 Hz, 6 H). |

TABLE 7

| Ex. | R₁ | R₂ | R₃ | R₄ | R₅ | ¹H-NMR (δ: ppm) [CDCl₃] |
|---|---|---|---|---|---|---|
| 32 | H | H | Cl | H | 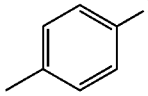 | 8.60 (s, 1 H), 8.27 (d, J=8.7 Hz, 1 H), 7.79 (d, J=1.7 Hz, 1H), 7.72 (d, J=7.9 Hz, 2 H), 7.59–7.56 (m, 2 H), 7.45 (dd, J=2.1, 8.7 Hz, 1 H), 7.35 (dd, J=2.5, 8.3 Hz, 2 H), 6.65 (d, J=8.7 Hz, 2 H), 4.03–3.95 (m, 4 H), 3.18 (d, J=22.0 Hz, 2 H), 3.04 (s, 6 H), 1.21 (t, J=7.1 Hz, 6 H). |
| 33 | H | H | Cl | H | 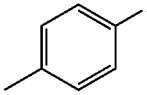 | 8.87 (s, 1 H), 8.26 (d, J=8.7 Hz, 1 H), 7.80 (d, J=1.7 Hz, 1 H), 7.67 (d, J=8.3 Hz, 2 H), 7.63–7.55 (m, 5 H), 7.47 (dd, J=2.1, 8.7 Hz, 1 H), 7.36 (dd, J=2.1, 8.3 Hz, 2 H), 4.05–3.97 (m, 4 H), 3.19 (d, J=22.0 Hz, 2 H), 2.19 (s, 3 H), 1.22 (t, J=7.1 Hz, 6 H). |
| 34 | H | H | Cl | H | 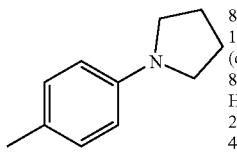 | 8.56 (s, 1 H), 8.27 (d, J=8.3 Hz, 1 H), 7.79 (d, J=2.1 Hz, 1 H), 7.72 (d, J=7.9 Hz, 2 H), 7.56 (d, J=8.7 Hz, 2 H), 7.44 (dd, J=2.1, 8.7 Hz, 1 H), 7.34 (dd, J=2.5, 8.3 Hz, 2 H), 6.51 (d, J=8.7 Hz, 2 H), 4.08–3.94 (m, 4 H), 3.39–3.33 (m, 4 H), 3.18 (d, J=21.6 Hz, 2 H), 2.05–2.02 (m, 4 H), 1.21(t, J=7.1 Hz, 6 H). |
| 35 | H | H | Cl | H | 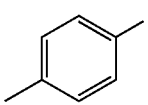 | 9.03 (s, 1 H), 8.29 (d, J=8.7 Hz, 1 H), 7.81 (d, J=2.1 Hz, 1 H), 7.77 (d, J=8.3 Hz, 2 H), 7.72 (d, J=7.5 Hz, 2 H), 7.66–7.59 (m, 4 H), 7.49–7.45 (m, 3 H), 7.42–7.38 (m, 3 H), 4.05–3.97 (m, 4 H), 3.20 (d, J=22.0 Hz, 2 H), 1.22 (t, J=7.1 Hz, 6 H). |
| 36 | H | H | Cl | H | 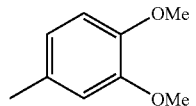 | 8.82 (s, 1 H), 8.28 (d, J=8.7 Hz, 1 H), 7.80 (d, J=2.1 Hz, 1 H), 7.71 (d, J=7.9 Hz, 2 H), 7.47 (dd, J=2.1, 8.7 Hz, 1 H), 7.37 (dd, J=2.5, 8.3 Hz, 2 H), 7.30 (d, J=1.7 Hz, 1 H), 7.23 (dd, J=1.7, 8.3 Hz, 1 H), 6.89 (d, J=8.3 Hz, 1 H), 4.05–3.95 (m, 4 H), 3.93 (s, 3 H), 3.84 (s, 3 H), 3.18 (d, J=22.0 Hz, 2 H), 1.21 (t, J=7.1 Hz, 6 H). |

TABLE 8

| Ex. | R₁ | R₂ | R₃ | R₄ | R₅ | ¹H-NMR (δ: ppm) [CDCl₃] |
|---|---|---|---|---|---|---|
| 37 | H | H | Cl | H | 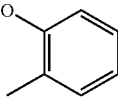 | 9.07 (s, 1 H), 8.28 (d, J=8.7 Hz, 1 H), 7.81–7.79 (m, 2 H), 7.70 (d, J=8.3 Hz, 2 H), 7.46–7.44 (m, 1 H), 7.36 (dd, J=2.5, 8.3 Hz, 2 H), 6.48 (dd, J=2.1, 8.7 Hz, 1 H), 6.43 (d, J=2.1 Hz, 1 H), 4.04–3.95 (m, 4 H), 3.85 (s, 3 H), 3.84 (s, 3 H), 3.18 (d, J=22.0 Hz, 2 H), 1.21 (t, J=7.1 Hz, 6 H). |
| 38 | H | H | Cl | H | 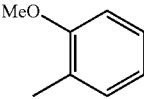 | 9.25 (s, 1 H), 8.29 (d, J=8.7 Hz, 1 H), 7.80 (d, J=2.1 Hz, 1 H), 7.70 (d, J=7.9 Hz, 2 H), 7.46 (dd, J=2.1, 8.7 Hz, 1 H), 7.36 (dd, J=2.5, 8.3 Hz, 2 H), 7.34 (d, J=2.9 Hz, 1 H), 7.03 (dd, J=2.9, 9.1 Hz, 1 H), 6.88 (d, J=9.1 Hz, 1 H), 4.04–3.95 (m, 4 H), 3.83 (s, 3 H), 3.71 (s, 3 H), 3.18 (d, J=21.6 Hz, 2 H), 1.21 (t, J=7.1 Hz, 6 H). |
| 39 | H | H | Cl | H | 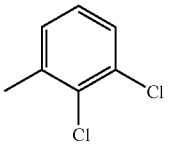 | 9.62 (s, 1 H), 8.30 (d, J=8.3 Hz, 1 H), 7.81 (d, J=2.1 Hz, 1 H), 7.70 (dd, J=1.2, 7.9 Hz, 1 H), 7.65 (d, J=7.9 Hz, 2 H), 7.58 (dd, J=1.2, 8.3 Hz, 1 H), 7.49 (dd, J=2.5, 8.7 Hz, 1 H), 7.39 (dd, J=2.5, 8.3 Hz, 2 H), 7.21 (t, J=7.9 Hz, 1 H), 4.06–3.99 (m, 4 H), 3.20 (d, J=21.6 Hz, 2 H), 1.23 (t, J=7.1 Hz, 6 H). |
| 40 | H | H | Cl | H | 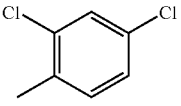 | 9.52 (s, 1 H), 8.29 (d, J=8.3 Hz, 1 H), 7.80 (d, J=2.1 Hz, 1 H), 7.73 (d, J=8.3 Hz, 1 H), 7.65 (d, J=7.9 Hz, 2 H), 7.50–7.47 (m, 2 H), 7.39 (dd, J=2.5, 8.3 Hz, 2 H), 7.24 (dd, J=2.1, 8.3 Hz, 1 H), 4.10–3.99 (m, 4 H), 3.20 (d, J=22.0 Hz, 2 H), 1.24 (t, J=7.1 Hz, 6 H). |
| 41 | H | H | Cl | H | 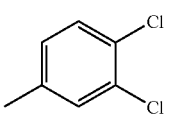 | 9.09 (s, 1 H), 8.27 (d, J=8.7 Hz, 1 H), 7.81 (d, J=2.1 Hz, 1 H), 7.77 (s, 1 H), 7.66 (d, J=7.5 Hz, 2 H), 7.50–7.47 (m, 3 H), 7.39 (dd, J=2.5, 8.3 Hz, 2 H), 4.08–3.99 (m, 4 H), 3.21 (d, J=22.0 Hz, 2 H), 1.24 (t, J=7.1 Hz, 6 H). |

TABLE 9

| Ex. | R₁ | R₂ | R₃ | R₄ | R₅ | ¹H-NMR (δ: ppm) [CDCl₃] |
|---|---|---|---|---|---|---|
| 42 | H | H | Cl | H | 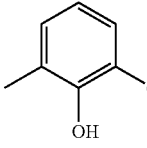 | 10.05 (s, 1 H), 9.07 (s, 1 H), 8.28 (d, J=8.3 Hz, 1 H), 7.80 (d, J=1.7 Hz, 1 H), 7.59 (d, J=7.9 Hz, 2 H), 7.49 (dd, J=2.1, 8.7 Hz, 1 H), 7.39 (dd, J=2.5, 8.3 Hz, 2 H), 7.01–6.98 (m, 2 H), 6.90 (t, J=7.9 Hz, 1 H), 4.06–3.93 (m, 4 H), 3.86 (s, 3 H), 3.19 (d, J=22.0 Hz, 2 H), 1.24 (t, J=7.1 Hz, 6 H). |
| 43 | H | H | Cl | H | 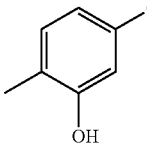 | 10.36 (s, 1 H), 8.89 (s, 1 H), 8.27 (d, J=8.3 Hz, 1 H), 7.80 (d, J=7.7 Hz, 1 H), 7.59 (d, J=7.9 Hz, 2 H), 7.49 (dd, J=2.1, 8.7 Hz, 1 H), 7.40 (dd, J=2.1, 8.3 Hz, 2 H), 7.22 (d, J=8.7 Hz, 1 H), 6.52 (dd, J=2.5, 8.7 Hz, 1 H), 6.37 (d, J=2.5 Hz, 1 H), 4.07–3.96 (m, 4 H), 3.82 (s, 3 H), 3.19 (d, J=22.0 Hz, 2 H), 1.24 (t, J=7.1 Hz, 6 H). |

TABLE 9-continued

| Ex. | R₁ | R₂ | R₃ | R₄ | R₅ | ¹H-NMR (δ: ppm) [CDCl₃] |
|---|---|---|---|---|---|---|
| 44 | H | H | Cl | H | 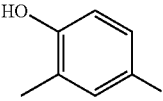 | 9.60 (s, 1 H), 9.07 (s, 1 H), 8.28 (d, 1 H), 7.81 (d, J=8.7 Hz, 1 H), 7.59 (d, J=7.9 Hz, 2 H), 7.50 (dd, J=2.1, 8.7 Hz, 1 H), 7.41 (dd, J=2.5, 8.3 Hz, 2 H), 7.00 (dd, J=2.9, 8.7 Hz, 1 H), 6.83–6.80 (m, 2 H), 4.06–3.96 (m, 4 H), 3.78 (s, 3 H), 3.21 (d, J=22.0 Hz, 2 H), 1.25 (t, J=7.1 Hz, 6 H). |
| 45 | H | H | Cl | H | 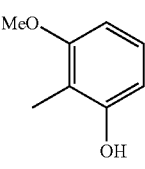 | 10.64 (s, 1 H), 9.41 (s, 1 H), 8.29 (d, J=8.7 Hz, 1 H), 7.80 (d, J=1.7 Hz, 1 H), 7.58 (d, J=7.9 Hz, 2 H), 7.49 (dd, J=2.1, 8.7 Hz, 1 H), 7.40 (dd, J=2.5, 8.3 Hz, 2 H), 7.30 (t, J=8.3 Hz, 1 H), 7.27–7.26 (m, 1 H), 6.46 (d, J=8.3 Hz, 1 H), 6.39 (d, 7.9 Hz, 1 H), 4.05–3.95 (m, 4 H), 3.86 (s, 3 H), 3.19 (d, J=22.0 Hz, 1 H), 1.23 (t, J=7.1 Hz, 6 H). |

TABLE 10

| Ex. | R₁ | R₂ | R₃ | R₄ | R₅ | ¹H-NMR (δ: ppm) [CDCl₃] |
|---|---|---|---|---|---|---|
| 46 | H | H | Cl | H | 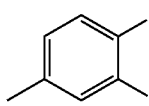 | 8.76 (s, 1 H), 8.27 (d, J=8.7 Hz, 1 H), 7.80 (d, J=2.1 Hz, 1 H), 7.69 (d, J=7.5 Hz, 2 H), 7.47 (dd, J=2.1, 6.2 Hz, 1 H), 7.45–7.29 (m, 8 H), 7.24 (dd, J=2.1, 8.3 Hz, 1 H), 6.91 (d, J=8.3 Hz, 1 H), 5.08 (s, 2 H), 4.03–3.94 (m, 4 H), 3.92 (s, 3 H), 3.16 (d, J=22.0 Hz, 2 H), 1.20 (t, J=7.1 Hz, 6 H). |
| 47 | H | H | Cl | H | 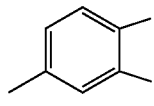 | 8.81 (s, 1 H), 8.27 (d, J=8.7 Hz, 1 H), 7.80 (d, J=2.1 Hz, 1 H), 7.68 (d, J=7.9 Hz, 2 H), 7.46 (dd, J=2.1, 8.3 Hz, 1 H), 7.37 (dd, J=2.5, 8.3 Hz, 2 H), 7.23 (d, J=1.7 Hz, 1 H), 7.14 (dd, J=1.7, 7.9 Hz, 1 H), 6.85 (d, J=7.9 Hz, 1 H), 6.02 (s, 2 H), 4.08–3.97 (m, 4 H), 3.20 (d, J=22.0 Hz, 2 H), 1.23 (t, J=7.1 Hz, 6 H). |
| 48 | H | H | Cl | H | 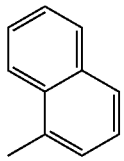 | 9.60 (s, 1 H), 8.51–8.49 (m, 1 H), 8.33 (d, J=8.3 Hz, 1 H), 8.00 (d, J=8.3 Hz, 1 H), 7.91–7.88 (m, 1 H), 7.86–7.83 (m, 2 H), 7.73 (d, J=8.3 Hz, 2 H), 7.56–7.49 (m, 4 H), 7.39 (dd, J=2.5, 8.3 Hz, 2 H), 4.02–3.93 (m, 4 H), 3.19 (d, J=22.0 Hz, 2 H), 1.17 (t, J=7.7 Hz, 6 H). |
| 49 | H | H | Cl | H | 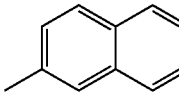 | 9.14 (s, 1 H), 8.30 (d, J=8.3 Hz, 1 H), 8.09 (s, 1 H), 7.89 (d, J=7.9 Hz, 1 H), 7.86–7.80 (m, 4 H), 7.73 (d, J=7.9 Hz, 2 H), 7.60–7.52 (m, 2 H), 7.48 (dd, J=2.1, 8.3 Hz, 1 H), 7.38 (dd, J=2.5, 8.3 Hz, 2 H), 4.03–3.94 (m, 4 H), 3.19 (d, J=22.0 Hz, 2 H), 1.19 (t, J=7.1 Hz, 6 H). |

TABLE 11

| Ex. | R₁ | R₂ | R₃ | R₄ | R₅ | ¹H-NMR (δ: ppm) [CDCl₃] |
|---|---|---|---|---|---|---|
| 50 | H | H | Cl | H | 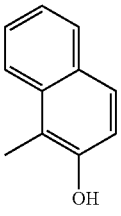 | 11.45(s, 1H), 9.97(S, 1H), 8.32 (d, J=8.7 Hz, 1H), 8.02(d, J= 8.7 Hz, 1H), 7.87(d, J=9.1 Hz, 1H), 7.83(d, J=1.7 Hz, 1H), 7.79 (d, J=7.9 Hz, 1H), 7.63(d, J= 7.9 Hz, 2H), 7.57(dt, J=1.2, 7.5 Hz, 1H), 7.52(dd, J=2.1, 8.3 Hz, 1H), 7.42–7.39(m, 3H), 7.06(d, J=9.1 Hz, 1H), 4.05–3.95(m, 4 H), 3.20(d, J=22.0 Hz, 2H), 1.23 (t, J=7.1 Hz, 6H). |
| 51 | H | H | Cl | H | 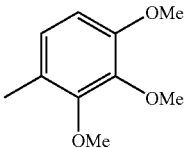 | 9.03(s, 1H), 8.28(d, J=8.3 Hz, 1H), 7.80(d, J=2.1 Hz, 1H), 7.69 (d, J=7.9 Hz, 2H), 7.57(d, J= 9.1 Hz, 1H), 7.46(dd, J=2.1, 8.7 Hz, 1H), 7.36(dd, J=2.5, 8.3 Hz, 2H), 6.68(d, J=8.7 Hz, 1H), 4.05–3.97(m, 4 H), 3.95(s, 3H), 3.90(s, 3H), 3.87(s, 3H), 3.18 (d, J=22.0 Hz, 2H), 1.22(t, J =7.1 Hz, 6H). |
| 52 | H | H | Cl | H | 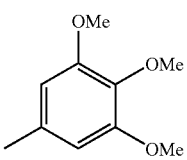 | 8.91(s, 1H), 8.28(d, J=8.7 Hz, 1H), 7.81(d, J=2.1 Hz, 1H), 7.71 (d, J=7.9 Hz, 2H), 7.48(dd, J= 2.1, 8.3 Hz, 1H), 7.38(dd, J= 2.5, 8.3 Hz, 2H), 6.95(s, 2H), 4.05–3.97(m, 4H), 3.90(s, 3H), 3.84(s, 6H), 3.18(d, J=22.0 Hz, 2H), 1.22(t, J=7.1 Hz, 6H). |
| 53 | H | H | Cl | H | 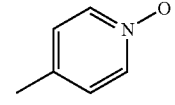 | 9.31(s, 1H), 8.27(d, J=8.3 Hz, 1H), 8.18(d, J=7.1 Hz, 2H), 7.81 (d, J=1.7 Hz, 1H), 7.63(d, J= 7.9 Hz, 2H), 7.52–7.48(m, 3H), 7.41(dd, J=2.5, 8.3 Hz, 2H), 4.10–4.02(m, 4H), 3.22(d,J=22.0 Hz, 2H), 1.27(t, J=7.1 Hz, 6H). |
| 54 | H | H | Cl | H | 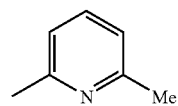 | 9.11(s, 1H), 8.29(d, J=8.7 Hz, 1H), 7.80(d, J=2.1 Hz, 1H), 7.68–7.65(m, 3H), 7.58(t, J=7.5 Hz, 1H), 7.47(dd, J=2.1. 8.7 Hz, 1H), 7.36(dd, J=2.5, 8.3 Hz, 2H), 7.23(d, J=7.5 Hz, 1H), 4.05–3.96(m, 4H), 3.19(d, J=22.0 Hz, 2H), 2.60(s, 3H), 1.22(t, J=7.1 Hz, 6H). |

TABLE 12

| Ex. | R₁ | R₂ | R₃ | R₄ | R₅ | ¹H-NMR (δ: ppm) [CDCl₃] |
|---|---|---|---|---|---|---|
| 55 | H | H | Cl | H | 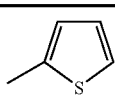 | 9.18(s, 1H), 8.27(d, J=8.7 Hz, 1H), 7.80(d, J=2.1 Hz, 1H), 7.71 (d, J=7.9 Hz, 2H), 7.52–7.49(m, 2H), 7.47(dd, J=2.1, 8.3 Hz, 1H), 7.39(dd, J=2.5, 8.3 Hz, 2H), 7.13(dd, J=3.7, 5.0 Hz, 1H), 4.06–3.70(m, 4H), 3.21(d, J=22.0 Hz, 2H), 1.24(t, J=7.1 Hz, 6H). |
| 56 | H | H | Cl | H | 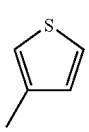 | 8.99(s, 1H), 8.27(d, J=8.3 Hz, 1H), 7.80(d, J=2.1 Hz, 1H), 7.79 (dd, J=0.8, 2.9 Hz, 1H), 7.69(d, J=7.9 Hz, 2H), 7.47(dd, J=2.1, 7.40–7.38(m, 2H), 7.36(d, J=2.5 Hz, 1H), 7.33(dd, J=2.9, 4.6 Hz, 1H), 4.06–3.98(m, 4H), 3.23(d, J=22.0 Hz, 2H), 1.23(t, J=7.1 Hz, 6H). |

TABLE 12-continued

| Ex. | R₁ | R₂ | R₃ | R₄ | R₅ | ¹H-NMR (δ: ppm) [CDCl₃] |
|---|---|---|---|---|---|---|
| 57 | H | H | Cl | H | 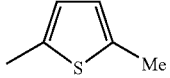 | 8.99(s, 1H), 8.27(d, J=8.7 Hz, 1H), 7.79(d, J=1.7 Hz, 1H), 7.71 (d, J=8.3 Hz, 2H), 7.46(dd, J= 2.1, 8.3 Hz, 1H), 7.38(dd, J= 2.5, 8.3 Hz, 2H), 7.30(d, J=3.3 Hz, 1H), 6.79(d, J=3.3 Hz, 1H), 4.07–3.98(m, 4H), 3.21(d, J=22.0 Hz, 2H), 2.50(s, 3H), 1.24(t, J=7.1 Hz, 6H). |
| 58 | H | H | Cl | H | 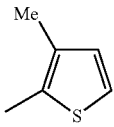 | 9.16(s, 1H), 8.26(d, J=8.3 Hz, 1H), 7.80(d, J=2.1 Hz, 1H), 7.72 (d, J=7.9 Hz, 2H), 7.46(dd, J= 2.1, 8.7 Hz, 1H), 7.42–7.37(m, H), 6.92(d, J=5.0 Hz, 1H), 4.06–3.97(m, 4H), 3.20(d, J=22.0 Hz, 2H), 2.40(s, 3H), 1.23(t, J=7.1 Hz, 6H). |
| 59 | H | H | Cl | H | 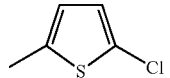 | 9.15(s, 1H), 8.26(d, J=8.3 Hz, 1H), 7.79(d, J=2.1 Hz, 1H), 7.67 (d, J=7.9 Hz, 2H), 7.47(dd, J= 2.1, 8.7 Hz, 1H), 7.40(dd, J= 2.5, 8.3 Hz, 2H), 7.27(d, J=3.7 Hz, 1H), 6.95(d, J=4.2 Hz, 1H), 4.08–4.01(m, 4H), 3.22(d, J=22.0 Hz, 2H), 1.27(t, J=7.1 Hz, 6H). |

TABLE 13

| Ex. | R₁ | R₂ | R₃ | R₄ | R₅ | ¹H-NMR (δ: ppm) [CDCl₃] |
|---|---|---|---|---|---|---|
| 60 | H | H | Cl | H | 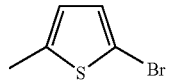 | 9.16(s, 1H), 8.25(d, J=8.3 Hz, 1H), 7.79(d, J=2.1 Hz, 1H), 7.67 (d, J=7.9 Hz, 2H), 7.47(dd, J= 2.1, 8.7 Hz, 1H), 7.40(dd, J= 2.5, 8.3 Hz, 2H), 7.24(d, J=4.2 Hz, 1H), 7.09(d, J=3.7 Hz, 1H), 4.11–3.98(m, 4H), 3.23(d, J=22.0 Hz, 2H), 1.26(t, J=7.1 Hz, 6H). |
| 61 | H | H | Cl | H | 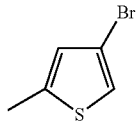 | 9.27(s, 1H), 8.26(d, J=8.7 Hz, 1H), 7.79(d, J=1.7 Hz, 1H), 7.67 (d, J=7.5 Hz, 2H), 7.47(dd, J= 2.1, 8.7 Hz, 1H), 7.40(d, J= 2.5 Hz, 1H), 7.39–7.38(m, 3H), 4.10–3.99(m, 4H), 3.21(d, J=22.0 Hz, 2H), 1.25(t, J=7.1 Hz, 6H). |
| 62 | H | H | Cl | H | 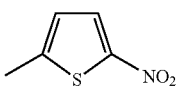 | 9.61(s, 1H), 8.26(d, J=8.3 Hz, 1H), 7.89(d, J=4.1 Hz, 1H), 7.81 (d, J=2.1 Hz, 1H), 7.65(d, J= 7.9 Hz, 2H), 7.50(dd, J=2.1, 8.3 Hz, 1H), 7.43(dd, J=2.5, 8.3 Hz, 2H), 7.39(d, J=4.1 Hz, 1H), 4.11–4.02(m, 4H), 3.24(d, J=22.4 Hz, 2H), 1.28(t, J=7.1 Hz, 6H). |
| 63 | H | H | Cl | H | 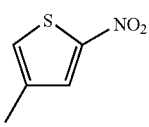 | 9.19(s, 1H), 8.26(d, J=8.7 Hz, 1H), 8.07(d, J=1.7 Hz, 1H), 7.88 (d, J=2.1 Hz, 1H), 7.81(d, J= 2.1 Hz, 1H), 7.65(d, J=7.9 Hz, 2H), 7.49(dd, J=2.1, 8.7 Hz, 1H), 7.41(dd, J=2.5, 8.3 Hz, 2H), 4.09–4.02(m, 4H), 3.22(d, J=22.0 Hz, 2H), 1.26(t, J=7.1 Hz, 6H). |

TABLE 13-continued

| Ex. | R₁ | R₂ | R₃ | R₄ | R₅ | ¹H-NMR (δ: ppm) [CDCl₃] |
|---|---|---|---|---|---|---|
| 64 | H | H | Cl | H | 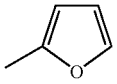 | 8.84(s, 1H), 8.26(d, J=8.7 Hz, 1H), 7.80(d, J=2.1 Hz, 1H), 7.69 (d, J=7.5 Hz, 2H), 7.60(d, J= 1.7 Hz, 1H), 7.47(dd, J=2.1, 8.3 Hz, 1H), 7.38(dd, J=2.5, 8.3 Hz, 1H), 6.98(d, J=3.7 Hz, 1H), 6.55 (dd,J=1.7, 3.7 Hz, 1H),4.07–3.99 (m, 4H), 3.20(d, J=22.0 Hz, 2H), 1.24(t, J=7.1 Hz, 6H). |

TABLE 14

| Ex. | R₁ | R₂ | R₃ | R₄ | R₅ | ¹H-NMR (δ: ppm) [CDCl₃] |
|---|---|---|---|---|---|---|
| 65 | H | H | Cl | H | 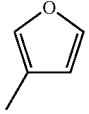 | 8.92(s, 1H), 8.26(d, J=8.7 Hz, 1H), 7.85(s, 1H), 7.79(d, J= 2.1 Hz, 1H), 7.6.8(d, J=7.9 Hz, 2H), 7.47(dd, J=2.1, 8.3 Hz, 1H), 7.44(s, 1H), 738(dd, J=2.5, 8.3 Hz, 2H), 6.65(d, J=1.7 Hz, 1H), 4.07–3.98(m, 4H), 3.20(d, J=22.0 Hz, 2H), 1.24(t, J=7.6 Hz, 6H). |
| 66 | H | H | Cl | H | 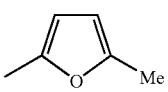 | 8.61(s, 1H), 8.26(d, J=8.3 Hz, 1H), 7.79(d, J=2.1 Hz, 1H), 7.70 (d, J=7.9 Hz, 2H), 7.45(dd, J= 2.1, 8.7 Hz, 1H), 7.37(dd, J= 2.5, 8.3 Hz, 2H), 6.89(d, J=3.3 Hz, 1H), 6.18(d, J=3.3 Hz, 1H), 4.06–3.96(m, 4H), 3.20(d, J=22.0 Hz, 2H), 2.37(s, 3H), 1.24(t, J=7.1 Hz, 6H). |
| 67 | H | H | Cl | H | 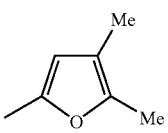 | 8.53(s, 1H), 8.25(d, J=8.7 Hz, 1H), 7.78(d, J=2.1 Hz, 1H), 7.69 (d, J=7.5 Hz, 2H), 7.45(dd, J= 2.1, 8.7 Hz, 1H), 7.37(dd, J= 2.5, 8.3 Hz, 2H), 6.78(s, 1H), 4.07–3.98(m, 4H), 3.19(d, J=22.0 Hz, 2H), 2.27(s, 3H), 1.99(s, 3H), 1.24(t, J=7.1 Hz, 6H). |
| 68 | H | H | Cl | H | 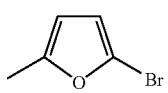 | 8.81(s, 1H), 8.25(d, J=8.7 Hz, 1H), 7.79(s, J=2.1 Hz, 1H), 7.68 (d, J=7.9 Hz, 2H), 7.46(dd, J= 2.1, 8.3 Hz, 1H), 7.39(dd, J= 2.5, 8.3 Hz, 2H), 6.90(d, J=3.3 Hz, 1H), 6.50(d, J=3.3 Hz, 1H), 4.07–4.00(m, 4H), 3.21(d, J=22.0 Hz, 2H), 1.24(t, J=7.1 Hz, 6H). |
| 69 | H | H | Cl | H | 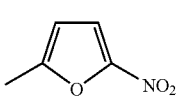 | 9.46(s, 1H), 8.27(d, J=8.3 Hz, 1H), 7.81(d, J=2.1 Hz, 1H), 7.67 (d, J=7.5 Hz, 2H), 7.50(dd, J= 2.1, 8.7 Hz, 1H), 7.42(dd, J= 2.5, 8.3 Hz, 2H), 7.35(d, J=4.2 Hz, 1H), 6.95(d, J=3.7 Hz, 1H), 4.10–4.02(m, 4H), 3.23(d, J=22.0 Hz, 2H), 1.27(t, J=7.1 Hz, 6H). |

TABLE 15

| Ex. | R₁ | R₂ | R₃ | R₄ | R₅ | ¹H-NMR (δ: ppm) [CDCl₃] |
|---|---|---|---|---|---|---|
| 70 | H | H | Cl | H | 2-methylbenzofuran-yl | 9.09(s, 1H), 8.28(d, J=8.3 Hz, 1H), 7.81(d, J=2.1 Hz, 1H), 7.72 (d, J=8.3 Hz, 2H), 7.66(d, J = 7.9 Hz, 1H), 7.51(d, J=8.3 Hz, 1H), 7.48(dd, J=2.1, 8.7 Hz, 1H), 7.44–7.37(m, 3H), 7.31–7.27 (m, 2H), 4.05–3.97(m, 4H), 3.20 (d, J=22.0 Hz, 2H), 1.21(t, J= 7.1 Hz, 6H). |
| 71 | H | H | Cl | H | 5-methyl-2-(4-chlorophenyl)furan-yl | 8.89(s, 1H), 8.27(d, J=8.7 Hz, 1H), 7.80(d, J=2.1 Hz, 1H), 7.74 (d, J=7.9 Hz, 2H), 7.66–7.62(m, 2H), 7.47(dd, J=2.1, 8.7 Hz, 1H), 7.40–7.38(m, 4H), 7.04(d, J= 3.7 Hz, 1H), 6.87(d, J=3.7 Hz, 1H), 4.04–3.97(m, 4H), 3.20(d, J=22.0 Hz, 2H), 1.21(t, J=7.1 Hz, 6H). |
| 72 | H | H | Cl | H | 2-methyl-1H-pyrrol-yl | 9.17(brs, 1H), 8.68(s, 1H), 8.27 (d, J=8.3 Hz, 1H), 7.79(d, J= 1.7 Hz, 1H), 7.64(d, J=7.9 Hz, 2H), 7.46(dd, J=1.7, 8.7 Hz, 1H), 7.37–7.35(m, 2H), 6.97(s, 1H), 6.72(s, 1H), 6.31–6.30(m, 1H), 4.06–3.99(m, 4H), 3.19(d, J= 22.0 Hz, 2H), 1.24(t, J=7.1 Hz, 6H). |
| 73 | H | H | Cl | H | 2-methyl-1-methyl-pyrrol-yl | 8.58(s, 1H), 8.27(d, J=8.7 Hz, 1H), 7.79(d, J=1.7 Hz, 1H), 7.64 (d, J=7.9 Hz, 2H), 7.46(dd, J= 2.1, 8.7 Hz, 1H), 7.36(dd, J= 2.5, 8.3 Hz, 2H), 6.80(t, J=1.7 Hz, 1H), 6.66(dd, J=1.7, 4.2 Hz, 1H), 6.18(dd, J=2.5, 4.2 Hz, 1H), 4.07–3.97(m, 4H), 3.63(s, 3H), 3.19(d, J=22.0 Hz, 2H), 1.24 (t, J=7.1 Hz, 6H). |
| 74 | H | H | Cl | H | 5-methyl-1H-imidazol-yl | 11.36(br, 1H), 8.92(br, 1H), 8.22 (d, J=8.7 Hz, 1H), 7.78(d, J= 2.1 Hz, 1H), 7.61(d, J=7.9 Hz, 2H), 7.50(br, 2H), 7.45(dd, J= 2.1, 8.3 Hz, 1H), 7.34(d, J= 5.8 Hz, 2H), 4.07–4.00(m, 4H), 3.20(d, J=22.0 Hz, 2H), 1.25(t, J=7.1 Hz, 6H). |

TABLE 16

| Ex. | R₁ | R₂ | R₃ | R₄ | R₅ | ¹H-NMR (δ: ppm) [CDCl₃] |
|---|---|---|---|---|---|---|
| 75 | H | H | Cl | H | 2-methyl-1H-imidazol-yl | 10.57(brs, 1H), 9.14(S, 1H), 8.24 (d, J=8.7 Hz, 1H), 7.77(d, J= 1.7 Hz, 1H), 7.60(d, J=7.5 Hz, 2H), 7.46(dd, J=2.1, 8.7 Hz, 1H), 7.35(dd, J=2.5, 8.7 Hz, 2H), 7.29(brs, 1H), 7.14(brs, 1H), 4.09–4.00(m, 4H), 3.22(d, J=21.6 Hz, 2H), 1.26(t, J=7.1 Hz, 6H). |
| 76 | H | H | Cl | H | 4,5-dimethyl-1H-imidazol-yl | 8.89(S, 1H), 8.23(d, J=8.3 Hz, 1H), 7.78(d, J=2.1 Hz, 1H), 7.62 (d, J=7.9 Hz, 2H), 7.46(dd, J= 2.1, 8.7 Hz, 1H), 7.43(brs, 1H), 7.35(dd, J=2.5, 8.3 Hz, 3H), 4.09–4.00(m, 4H), 3.20(d, J=22.0 Hz, 2H), 2.37(s, 3H), 1.21(t, J=7.1 Hz, 6H). |

TABLE 16-continued

| Ex. | R₁ | R₂ | R₃ | R₄ | R₅ | ¹H-NMR (δ: ppm) [CDCl₃] |
|---|---|---|---|---|---|---|
| 77 | H | Cl | H | H | 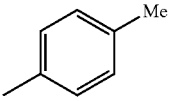 | 8.89(s, 1H), 8.31(d, J=2.1 Hz, 1H), 7.73–7.72(m, 2H), 7.69(d, J=8.3 Hz, 2H), 7.59(d, J=8.3 Hz, 2H), 7.36(dd, J=2.5, 8.3 Hz, 2H), 7.22(d, J=8.3 Hz, 2H), 4.04–3.95(m, 4H), 3.19(d, J=22.0 Hz, 2H), 2.40(s, 3H), 1.21(t, J=7.1 Hz, 6H). |
| 78 | H | Cl | H | H | 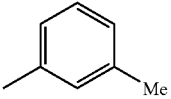 | 8.90(s, 1H), 8.31(d, J=2.5 Hz, 1H), 7.76–7.69(m, 4H), 7.52–7.47(m, 2H), 7.37(dd, J=2.5, 8.3 Hz, 2H), 7.33–7.28(m, 2H), 4.06–3.93(m, 4H), 3.19(d, J=22.0 Hz, 2H), 2.37(s, 3H), 1.21(t, J=7.1 Hz, 6H). |
| 79 | H | Cl | H | H | 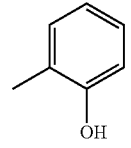 | 10.01(s, 1H), 9.09(s, 1H), 8.31(t, J=1.7 Hz, 1H), 7.75(d, J=1.7 Hz, 2H), 7.59(d, J=7.9 Hz, 2H), 7.42–7.40(m, 4H), 7.37–7.34(m, 1H), 6.97(t, J=7.1 Hz, 1H), 6.88(d, J=8.3 Hz, 1H), 4.08–3.94(m, 4H), 3.20(d, J=22.0 Hz, 2H), 1.24(t, J=7.1 Hz, 6H). |
| 80 | H | Cl | H | H | 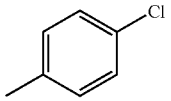 | 9.03(s, 1H), 8.30(d, J=2.1 Hz, 1H), 7.76–7.73(m, 2H), 7.68–7.61(m, 4H), 7.41–7.36(m, 4H), 4.06–3.97(m, 4H), 3.20(d, J=22.0 Hz, 2H), 1.22(t, J=7.1 Hz, 6H). |

TABLE 17

| Ex. | R₁ | R₂ | R₃ | R₄ | R₅ | ¹H-NMR (δ: ppm) [CDCl₃] |
|---|---|---|---|---|---|---|
| 81 | H | Cl | H | H | 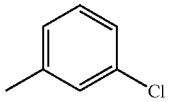 | 9.04(s, 1H), 8.30(dd, J=0.8, 2.1 Hz, 1H), 7.75(dd, J=0.8, 8.7 Hz, 1H), 7.72(dd, J=2.1, 8.7 Hz, 1H), 7.69(d, J=2.1 Hz, 1H), 7.68(d, J=7.5 Hz, 2H), 7.56(td, J=1.2, 7.9 Hz, 1H), 7.47(ddd, J=1.2, 2.1, 7.9 Hz, 1H), 7.38(dd, J=2.5, 8.3 Hz, 2H), 7.35(t, J=7.9 Hz, 1H), 4.07–3.97(m, 4H), 3.21(d, J=22.0 Hz, 2H), 1.23(t, J=7.1 Hz, 6H). |
| 82 | H | Cl | H | H | 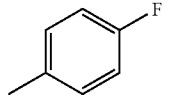 | 8.98(s, 1H), 8.31(d, J=2.1 Hz, 1H), 7.76–7.70(m, 4H), 7.68(d, J=7.9 Hz, 2H), 7.37(dd, J=2.5, 8.3 Hz, 2H), 7.10(t, J=8.5 Hz, 2H), 4.05–3.97(m, 4H), 3.19(d, J=21.6 Hz, 2H), 1.22(t, J=7.1 Hz, 6H). |
| 83 | H | Cl | H | H | 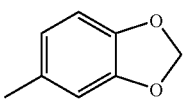 | 8.81(s, 1H), 8.30(d, J=2.1 Hz, 1H), 7.75–7.67(m, 4H), 7.37(dd, J=2.5, 8.3 Hz, 2H), 7.23(d, J=1.2 Hz, 1H), 7.15(dd, J=1.7, 7.9 Hz, 1H), 6.85(d, J=8.3 Hz, 1H), 6.02(s, 2H), 4.06–3.97(m, 4H), 3.20(d, J=22.0 Hz, 2H), 1.23(t, J=7.1 Hz, 6H). |
| 84 | H | Cl | H | H | 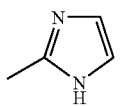 | 10.05(br, 1H), 9.14(s, 1H), 8.20(s, 1H), 7.72(s, 2H), 7.59(d, J=8.3 Hz, 2H), 7.35(dd, J=2.1, 8.3 Hz, 2H), 7.31(s, 1H), 7.14(s, 1H), 4.09–4.01(m, 4H), 3.20(d, J=21.6 Hz, 2H), 1.26(t, J=7.1 Hz, 6H). |

TABLE 17-continued

| Ex. | R₁ | R₂ | R₃ | R₄ | R₅ | ¹H-NMR (δ: ppm) [CDCl₃] |
|---|---|---|---|---|---|---|
| 85 | H | Cl | H | H | 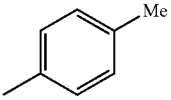 | 8.88(s, 1H), 7.72–7.69(m, 3H), 7.62(t, J=7.9 Hz, 1H), 7.59(d, J=8.3 Hz, 2H), 7.51(dd, J=1.2, 7.5 Hz, 1H), 7.36(dd, J=2.5, 8.3 Hz, 2H), 7.21(d, J=7.9 Hz, 2H), 4.05–3.95(m, 4H), 3.18(d, J=22.0 Hz, 2H), 2.39(s, 3H), 1.21(t, J=7.1 Hz, 6H). |

TABLE 18

| Ex. | R₁ | R₂ | R₃ | R₄ | R₅ | ¹H-NMR (δ: ppm) [CDCl₃] |
|---|---|---|---|---|---|---|
| 86 | Cl | H | H | H | 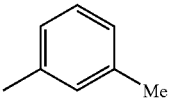 | 8.89(s, 1H), 7.71(d, J=8.3 Hz, 3H), 7.63(t, J=7.9 Hz, 1H), 7.53–7.49(m, 3H), 7.37(dd, J=2.5, 8.3 Hz, 2H), 7.30–7.29(m, 2H), 4.05–3.95(m, 4H), 3.19(d, J=22.0 Hz, 2H), 2.36(s, 3H), 1.21(t, J=7.1 Hz, 6H). |
| 87 | Cl | H | H | H | 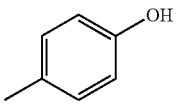 | 8.64(s, 1H), 8.22(brs, 1H), 7.71–7.69(m, 3H), 7.61(t, J=7.9 Hz, 1H), 7.49(d, J=7.5 Hz, 1H), 7.45(d, J=8.3 Hz, 2H), 7.34(d, J=8.3 Hz, 2H), 6.72(d, J=8.7 Hz, 2H), 4.03–3.94(m, 4H), 3.20(d, J=22.0 Hz, 2H), 1.20(t, J=7.1 Hz, 6H). |
| 88 | Cl | H | H | H | 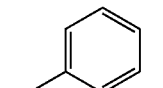 | 10.06(s, 1H), 9.06(s, 1H), 7.72(dd, J=1.2, 7.9 Hz, 1H), 7.66(t, J=7.9 Hz, 1H), 7.59(d, J=7.9 Hz, 2H), 7.55(dd, J=1.2, 7.9 Hz, 1H), 7.42–7.35(m, 4H), 6.96(t, J=7.5 Hz, 1H), 6.87(d, J=8.7 Hz, 1H), 4.06–3.96(m, 4H), 3.20(d, J=22.0 Hz, 2H), 1.24(t, J=7.1 Hz, 6H). |
| 89 | Cl | H | H | H | 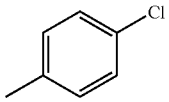 | 9.01(s, 1H), 7.71(dd, J=1.2, 7.9 Hz, 1H), 7.67(d, J=7.9 Hz, 2H), 7.64–7.61(m, 3H), 7.52(dd, J=1.2, 7.9 Hz, 1H), 7.39–7.36(m, 4H), 4.06–3.98(m, 4H), 3.19(d, J=22.0 Hz, 2H), 1.22(t, J=7.1 Hz, 6H). |
| 90 | Cl | H | H | H | 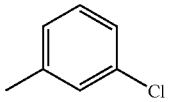 | 9.02(s, 1H), 7.71(dd, J=1.2, 8.3 Hz, 1H), 7.68(d, J=8.3 Hz, 3H), 7.66(t, J=7.9 Hz, 1H), 7.56(d, J=7.9 Hz, 1H), 7.52(d, J=1.2, 7.9 Hz, 1H), 7.47–7.45(dd, 1H), 7.39(m, J=2.5, 8.3 Hz, 2H), 7.35(t, J=7.9 Hz, 1H), 4.06–3.98(m, 4H), 3.20(d, J=22.0 Hz, 2H), 1.23(t, J=7.1 Hz, 6H). |

TABLE 19

| Ex. | R₁ | R₂ | R₃ | R₄ | R₅ | ¹H-NMR (δ: ppm) [CDCl₃] |
|---|---|---|---|---|---|---|
| 91 | Cl | H | H | H | 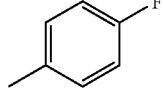 | 8.97(s, 1H), 7.72–7.68(m, 5H), 7.64(t, J=7.9 Hz, 1H), 7.52(dd, J=1.2, 7.9 Hz, 1H), 7.37(dd, J=2.5, 8.3 Hz, 2H), 7.09(t, J=8.7 Hz, 2H), 4.06–3.97(m, 4H), 3.19(d, J=22.0 Hz, 2H), 1.22(t, J=7.1 Hz, 6H). |

TABLE 19-continued

| Ex. | R₁ | R₂ | R₃ | R₄ | R₅ | ¹H-NMR (δ: ppm) [CDCl₃] |
|---|---|---|---|---|---|---|
| 92 | Cl | H | H | H | 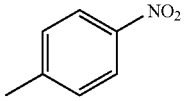 | 9.38(s, 1H), 8.26(d, J=8.7 Hz, 2H), 7.82(d, J=8.7 Hz, 2H), 7.73 (dd, J=1.2, 7.9 Hz, 1H), 7.69–7.65 (m, 3H), 7.55(dd, J=1.2, 7.5 Hz, 1H), 7.40(dd, J=2.5, 8.3 Hz, 2H), 4.09–4.01(m, 4H), 3.21(d, J=22.0 Hz, 2H), 1.25(t, J=7.1 Hz, 6H). |
| 93 | Cl | H | H | H | 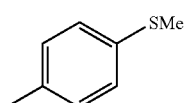 | 8.89(s, 1H), 7.72–7.68(m, 3H), 7.64(d, J=7.9 Hz, 1H), 7.60(d, J=8.3 Hz, 2H), 7.51(dd, J=1.2, 7.5 Hz, 1H), 7.36(dd, J=2.5, 8.3 Hz, 2H), 7.22(d, J=8.7 Hz, 2H), 4.05–3.96(m, 4H), 3.19(d, J=22.0 Hz, 2H), 2.51(s, 3H), 1.22(t, J=7.1 Hz, 6H). |
| 94 | Cl | H | H | H | 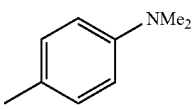 | 8.60(s, 1H), 7.72(d, J=7.5 Hz, 2H), 7.69(dd, J=1.2, 8.3 Hz, 1H), 7.63–7.56(m, 3H), 7.49(dd, J=1.2, 7.5 Hz, 1H), 7.34(dd, J=2.5, 8.3 Hz, 2H), 6.64(d, J=8.7 Hz, 2H), 4.04–3.94(m, 4H), 3.17(d, J=22.0 Hz, 2H), 3.04(s, 6H), 1.21(t, J=7.1 Hz, 6H). |
| 95 | Cl | H | H | H | 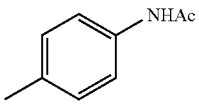 | 8.84(s, 1H), 7.72–7.60(m, 7 H), 7.55(d, J=8.7 Hz, 2H), 7.50(dd, J=1.2, 7.5 Hz, 1H), 7.35(dd, J=2.5, 8.3 Hz, 2H), 4.05–3.95(m, 4H), 3.19(d, J=22.0 Hz, 2H), 2.19(s, 3H), 1.22(t, J=7.1 Hz, 6H). |

TABLE 20

| Ex. | R₁ | R₂ | R₃ | R₄ | R₅ | ¹H-NMR (δ: ppm) [CDCl₃] |
|---|---|---|---|---|---|---|
| 96 | Cl | H | H | H | 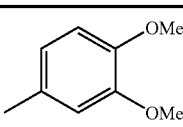 | 8.82(s, 1H), 7.72(d, J=7.9 Hz, 2H), 7.71(dd, J=1.7, 7.9 Hz, 1H), 7.63(t, J=7.9 Hz, 1H), 7.51 (dd, J=1.2, 7.5 Hz, 1H), 7.36(dd, J=2.5, 8.3 Hz, 2H), 7.30(d, J=2.1 Hz, 1H), 7.23(dd, J=1.7, 8.3 Hz, 1H), 6.88(d, J=8.3 Hz, 1H), 4.04–3.95(m, 4H), 3.93(s, 3H), 3.84(s, 3H), 3.17(d, J=22.0 Hz, 2H), 1.21(t, J=7.1 Hz, 6H). |
| 97 | Cl | H | H | H | 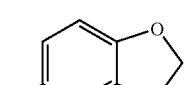 | 8.80(s, 1H), 7.31–7.68(m, 3H), 7.63(t, J=7.9 Hz, 1H), 7.51(dd, J=1.2, 7.5 Hz, 1H), 7.37(dd, J=2.5, 8.3 Hz, 2H), 7.23(d, J=1.7 Hz, 1H), 7.15(dd, J=1.7, 7.9 Hz, 1H), 6.84(d, J=7.9 Hz, 1H), 6.02(s, 2H), 4.06–3.97(m, 4H), 3.20(d, J=22.0 Hz, 2H), 1.22(t, J=7.1 Hz, 6H). |
| 98 | Cl | H | H | H | 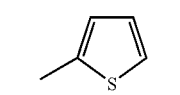 | 9.16(s, 1H), 7.73–7.69(m, 3H), 7.63(t, J=7.9 Hz, 1H), 7.51(d, J=5.8 Hz, 2H), 7.49(d, J=4.2 Hz, 1H), 7.38(dd, J=2.5, 8.3 Hz, 2H), 7.12(dd, J=3.7, 5.0 Hz, 1H), 4.06–3.97(m, 4H), 3.23(d, J=22.0 Hz, 2H), 1.24(t, J=7.1 Hz, 6H). |

TABLE 20-continued

| Ex. | R₁ | R₂ | R₃ | R₄ | R₅ | ¹H-NMR (δ: ppm) [CDCl₃] |
|---|---|---|---|---|---|---|
| 99 | Cl | H | H | H | 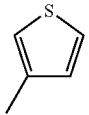 | 8.98(s, 1H), 7.78(dd, J=1.2, 2.9 Hz, 1H), 7.72–7.69(m, 3H), 7.63(t, J=7.9 Hz, 1H), 7.52(dd, J=1.2, 7.9 Hz, 1H), 7.40–7.36(m, 3H), 7.33–7.30(m, 1H), 4.06–3.97 (m, 4H), 3.22(d, J=22.0 Hz, 2H), 1.23(t, J=7.1 Hz, 6H). |
| 100 | Cl | H | H | H | 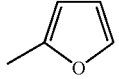 | 8.82(s, 1H), 7.70(dd, J=0.8, 8.3 Hz, 3H), 7.63(t, J=7.9 Hz, 1H), 7.59(d, J=1.7 Hz, 1H), 7.51 (dd, J=1.2, 7.9 Hz, 1H), 7.37(dd, 2.5, 8.3 Hz, 2H), 6.97(d, J= 3.3 Hz, 1H), 6.55(dd, J=1.7, 3.3 Hz, 1H), 4.07–3.98(m, 4H), 3.20(d, J=22.0 Hz, 2H), 1.24(t, J=7.1 Hz, 6H). |

TABLE 21

| Ex. | R₁ | R₂ | R₃ | R₄ | R₅ | ¹H-NMR(δ:ppm) [CDCl₃] |
|---|---|---|---|---|---|---|
| 101 | Cl | H | H | H | 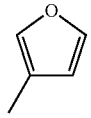 | 8.90 (s, 1 H), 7.84 (s, 1 H), 7.70 (dd, J = 1.2, 7.9 Hz, 2 H), 7.68 (d, J = 5.4 Hz, 1 H), 7.63 (t, J = 7.9 Hz, 1H), 7.51 (dd, J = 1.2, 7.9 Hz, 1H), 7.43 (t, J = 1.7 Hz, 1 H), 7.37 (dd, J = 2.1, 8.3 Hz, 2 H), 6.65 (d, J = 1.7 Hz, 1 H), 4.07–3.98 (m, 4 H), 3.20 (d, J = 22.0 Hz, 2 H), 1.24 (t, J = 7.1 Hz, 6 H). |
| 102 | Cl | H | H | H | 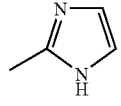 | 10.97 (br, 1 H), 9.02 (s, 1 H), 7.68 (dd, J = 1.2, 8.3 Hz, 1 H), 7.62 (t, J = 7.9 Hz, 1 H), 7.60 (d, J = 8.3 Hz, 2 H), 7.50 (dd, J = 1.2, 7.9 Hz, 1 H), 7.34 (dd, J = 2.5, 8.3 Hz, 2 H), 7.29 (brs, 1 H), 7.12 (brs, 1 H), 4.08–3.99 (m, 4 H), 3.18 (d, J = 21.6 Hz, 2 H), 1.26 (t, J = 7.1 Hz, 6 H). |
| 103 | H | H | H | H | 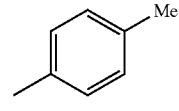 | 8.93 (s, 1 H), 8.36 (d, J = 7.9 Hz, 1 H), 7.82–7.77 (m, 2 H), 7.70 (d, J = 7.9 Hz, 2 H), 7.59 (d, J = 8.3 Hz, 2 H), 7.53 (ddd, J = 2.1, 5.8, 8.3 Hz, 1 H), 7.36 (dd, J = 2.5, 8.3 Hz, 2 H), 7.21 (d, J = 7.9 Hz, 2 H), 4.05–3.95 (m, 4H), 3.19 (d, J = 22.0 Hz, 2 H), 2.39 (s, 3 H), 1.22 (t, J = 7.1 Hz, 6 H). |
| 104 | H | H | H | H | 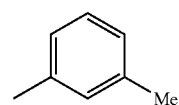 | 8.94 (s, 1 H), 8.37–8.35 (m, 1 H), 7.82–7.77 (m, 2H), 7.71 (d, J = 7.9 Hz, 2 H), 7.55–7.49 (m, 3 H), 7.37 (dd, J = 2.5, 8.3 Hz, 2H), 7.31–7.27 (m, 2 H), 4.05–3.95 (m, 4 H), 3.19 (d, J = 22.0 Hz, 2 H), 2.37 (s, 3 H), 1.21 (t, J = 7.1 Hz, 6 H). |
| 105 | H | H | H | H | 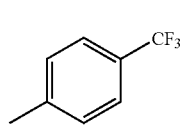 | 9.28 (s, 1 H), 8.36 (d, J = 7.9 Hz, 1H), 7.82–7.78 (m, 4H), 7.69–7.66 (m, 4 H), 7.57–7.53 (m, 1 H), 7.39 (dd, J = 2.5, 8.3 Hz, 2H), 4.08–3.99 (m, 4 H), 3.21 (d, J = 22.0 Hz, 2 H), 1.23 (t, J = 7.1 Hz, 6 H). |

TABLE 22

| Ex. | R₁ | R₂ | R₃ | R₄ | R₅ | ¹H-NMR(δ:ppm) [CDCl₃] |
|---|---|---|---|---|---|---|
| 106 | H | H | H | H | 4-HO-C₆H₄- | 8.67 (s, 1 H), 8.34 (d, J = 7.9 Hz, 1 H), 8.15 (br, 1 H), 7.82–7.76 (m, 2 H), 7.69 (d, J = 7.9 Hz, 2 H), 7.54–7.50 (m, 1 H), 7.47 (d, J = 8.7 Hz, 2 H), 7.35 (dd, J = 2.5, 8.3 Hz, 2 H), 6.76 (d, J = 8.7 Hz, 2 H), 4.03–3.93 (m, 4 H), 3.20 (d, J = 22.0 Hz, 2 H), 1.21 (t, J = 7.1 Hz, 6 H). |
| 107 | H | H | H | H | 2-HO-C₆H₄- | 10.08 (s, 1 H), 9.13 (s, 1 H), 8.36 (d, J = 7.9 Hz, 1 H), 7.85–7.80 (m, 2 H), 7.60 (d, J = 7.4 Hz, 2 H), 7.58–7.54 (m, 1 H), 7.41 (dd, J = 2.5, 8.3 Hz, 2 H), 7.38–7.34 (m, 2 H), 6.96 (t, J = 7.9 Hz, 1 H), 6.87 (d, J = 8.3 Hz, 1 H), 4.06–3.96 (m, 4 H), 3.23 (d, J = 22.0 Hz, 2 H), 1.23 (t, J = 7.1 Hz, 6 H). |
| 108 | H | H | H | H | 4-Cl-C₆H₄- | 9.07 (s, 1 H), 8.35 (d, J = 7.5 Hz, 1 H), 7.83–7.76 (m, 2 H), 7.67 (d, J = 7.9 Hz, 2 H), 7.63–7.61 (m, 2 H), 7.57–7.52 (m, 1 H), 7.40–7.36 (m, 4 H), 4.09–3.95 (m, 4 H), 3.20 (d, J = 22.0 Hz, 2 H), 1.23 (t, J = 7.1 Hz, 6 H). |
| 109 | H | H | H | H | 3-Cl-C₆H₄- | 9.08 (s, 1 H), 8.37 (d, J = 7.9 Hz, 1 H), 7.82–7.80 (m, 2 H), 7.69–7.67 (m, 3 H), 7.56–7.52 (m, 2 H), 7.47–7.45 (m, 1 H), 7.40–7.34 (m, 3 H), 4.06–3.98 (m, 4 H), 3.21 (d, J = 22.0 Hz, 2 H), 1.23 (t, J = 7.1 Hz, 6 H). |
| 110 | H | H | H | H | 4-F-C₆H₄- | 9.03 (s, 1 H), 8.36 (d, J = 7.9 Hz, 1 H), 7.82–7.77 (m, 2 H), 7.72–7.68 (m, 4 H), 7.53 (ddd, J = 2.5, 5.8, 8.3 Hz, 1 H), 7.37 (dd, J = 2.5, 8.3 Hz, 2 H), 7.13–7.08 (m, 2 H), 4.06–3.97 (m, 4 H), 3.20 (d, J = 22.0 Hz, 2H), 1.23 (t, J = 7.1 Hz, 6 H). |

TABLE 23

| Ex. | R₁ | R₂ | R₃ | R₄ | R₅ | ¹H-NMR(δ:ppm) [CDCl₃] |
|---|---|---|---|---|---|---|
| 111 | H | H | H | H | 3-F-C₆H₄- | 9.14 (d, J = 0.8 Hz, 1 H), 8.36 (d, J = 7.5 Hz, 1 H), 7.83–7.78 (m, 2 H), 7.68 (d, J = 7.9 Hz, 2 H), 7.54 (ddd, J = 2.9, 5.4, 8.3 Hz, 1 H), 7.45–7.37 (m, 5 H), 7.21–7.16 (m, 1 H), 4.07–3.99 (m, 4 H), 3.21 (d, J = 22.0 Hz, 2 H), 1.23 (t, J = 7.1 Hz, 6 H). |
| 112 | H | H | H | H | 4-O₂N-C₆H₄- | 9.47 (s, 1 H), 8.36 (d, J = 7.9 Hz, 1 H), 8.26 (d, J = 9.1 Hz, 2 H), 7.83–7.80 (m, 4 H), 7.67 (d, J = 7.5 Hz, 2 H), 7.58–7.54 (m, 1 H), 7.40 (dd, J = 2.5, 8.3 Hz, 2 H), 4.10–4.01 (m, 4 H), 3.22 (d, J = 22.0 Hz, 2 H), 1.26 (t, J = 7.1 Hz, 6 H). |
| 113 | H | H | H | H | 4-MeS-C₆H₄- | 8.93 (s, 1 H), 8.36 (d, J = 8.3 Hz, 1 H), 7.82–7.77 (m, 2 H), 7.69 (d, J = 7.9 Hz, 2 H), 7.60 (d, J = 8.3 2 H), 7.53 (ddd, J = 2.5, 5.8, 8.3 Hz, 1 H), 7.36 (dd, J = 2.5, 8.3 Hz, 2 H), 7.23 (d, J = 8.3 Hz, 2H), 4.05–3.96 (m, 4 H), 3.19 (d, J = 22.0 Hz, 2 H), 2.51 (s, 3 H), 1.22 (t, J = 7.1 Hz, 6 H). |

TABLE 23-continued

| Ex. | R₁ | R₂ | R₃ | R₄ | R₅ | ¹H-NMR(δ:ppm) [CDCl₃] |
|---|---|---|---|---|---|---|
| 114 | H | H | H | H | 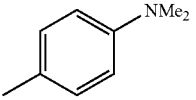 | 8.63 (s, 1 H), 8.36 (d, J = 7.5 Hz, 1 H), 7.81–7.75 (m, 2 H), 7.72 (d, J = 7.9 Hz, 2 H), 7.58 (d, J = 8.7 Hz, 2 H), 7.51 (ddd, J = 1.7, 6.2, 8.3 Hz, 1H), 7.34 (dd, J = 2.5, 8.3 Hz, 2H), 6.65 (d, J = 9.1 Hz, 2H), 4.04–3.94 (m, 4H), 3.18 (d, J = 22.0 Hz, 2 H), 3.04 (s, 6 H), 1.21 (t, J = 7.1 Hz, 6 H). |
| 115 | H | H | H | H | 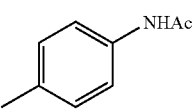 | 8.89 (s, 1 H), 8.35 (d, J = 7.5 Hz, 1 H), 7.82–7.77 (m, 2 H), 7.68 (d, J = 7.9 Hz, 2 H), 7.63–7.51 (m, 6 H), 7.36 (dd, J = 2.5, 8.3 Hz, 2 H), 4.05–3.96 (m, 4H), 3.19 (d, J = 22.0 Hz, 2 H), 2.22 (s, 3 H), 1.22 (t, J = 7.1 Hz, 6 H). |

TABLE 24

| Ex. | R₁ | R₂ | R₃ | R₄ | R₅ | ¹H-NMR(δ:ppm) [CDCl₃] |
|---|---|---|---|---|---|---|
| 116 | H | H | H | H | 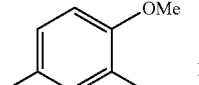 | 8.86 (s, 1 H), 8.36 (d, J = 7.9 Hz, 1 H), 7.82–7.77 (m, 2 H), 7.72 (d, J = 7.5 Hz, 2 H), 7.55–7.51 (m, 1 H), 7.36 (dd, J = 2.5, 8.3 Hz, 2 H), 7.30 (d, J = 1.7 Hz, 1H), 7.23 (dd, J = 1.7, 8.3 Hz, 1 H), 6.89 (d, J = 8.3 Hz, 1 H), 4.05–3.95 (m, 4 H), 3.93 (s, 3 H), 3.84 (s, 3 H), 3.18 (d, J = 22.0 Hz, 2 H), 1.21 (t, J = 7.1 Hz, 6 H). |
| 117 | H | H | H | H | 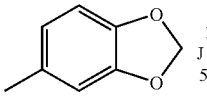 | 8.85 (s, 1 H), 8.35 (d, J = 7.5 Hz, 1 H), 7.82–7.76 (m, 2 H), 7.69 (d, J = 7.5 Hz, 2 H), 7.52 (ddd, J = 2.5, 5.8, 8.3 Hz, 1 H), 7.37 (dd, J = 2.5, 8.3 Hz, 2 H), 7.23 (d, J = 1.2 Hz, 1 H), 7.14 (dd, J = 1.2, 8.3 Hz, 1 H), 6.85 (d, J = 8.3 Hz, 1 H), 6.02 (s, 2 H), 4.06–3.97 (m, 4 H), 3.20 (d, J = 22.0 Hz, 2 H), 1.32 (t, J = 7.1 Hz, 6 H). |
| 118 | H | H | H | H | 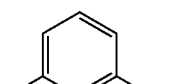 | 9.14 (s, 1 H), 8.37 (d, J = 7.5 Hz, 1 H), 7.82–7.79 (m, 2 H), 7.68 (d, J = 7.5 Hz, 2 H), 7.66 (d, J = 8.3 7.55–7.51 (m, 1 H), 7.36 (dd, J = 2.5, 8.3 Hz, 2 H), 7.22 (d, J = 7.5 Hz, 1 H), 4.06–3.96 (m, 4 H), 3.19 (d, J = 22.0 Hz, 2 H), 2.60 (s, 3 H), 1.22 (t, J = 7.1 Hz, 6 H). |
| 119 | H | H | H | H | 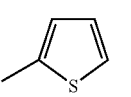 | 9.22 (s, 1 H), 8.35 (d, J = 7.5 Hz, 1 H), 7.82–7.67 (m, 2 H), 7.72 (d, J = 7.5 Hz, 2 H), 7.55–7.49 (m, 3 H), 7.38 (dd, J = 2.5, 8.3 Hz, 2 H), 7.13 (dd, J = 3.7, 5.0 Hz, 1 H), 4.06–3.98 (m, 4 H), 3.21 (d, 2 H), 1.24 (t, J = 7.1 Hz, 6 H). |
| 120 | H | H | H | H | 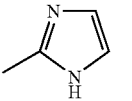 | 10.04 (br, 1 H), 9.18 (s, 1 H), 8.35 (d, J = 7.9 Hz, 1 H), 7.79 (d, J = 3.7 Hz, 2 H), 7.60 (d, J = 7.9 Hz, 2 H), 7.55–7.51 (m, 1 H), 7.35 (dd, J = 2.5, 8.3 Hz, 2 H), 7.30 (brs, 1 H), 7.13 (brs, 1 H), 4.09–4.01 (m, 4 H), 3.20 (d, J = 22.0 Hz, 2 H), 1.27 (t, J = 7.1 Hz, 6 H). |

TABLE 25

| Ex. | R₁ | R₂ | R₃ | R₄ | R₅ | ¹H-NMR(δ:ppm) [CDCl₃] |
|---|---|---|---|---|---|---|
| 121 | H | Me | H | H | 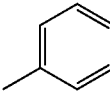 | 9.18 (s, 1 H), 8.14 (s, 1 H), 7.72–7.66 (m, 3 H), 7.63–7.58 (m, 2 H), 7.53 (brs, 1 H), 7.45 (t, J = 7.9 Hz, 1 H), 7.38 (dd, J = 2.5, 8.3 Hz, 2 H), 7.34–7.31 (m, 1 H), 4.06–3.97 (m, 4 H), 3.20 (d, J = 22.0 Hz, 2 H), 2.53 (s, 3 H), 1.23 (t, J = 7.1 Hz, 6 H). |
| 122 | H | Me | H | H | 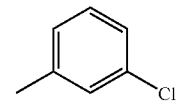 | 9.08 (s, 1 H), 8.14 (s, 1 H), 7.72–7.66 (m, 4 H), 7.61 (dd, J = 2.1, 8.3 Hz, 1 H), 7.55 (d, J = 7.9 Hz, 1 H), 7.46–7.44 (m, 1 H), 7.38 (dd, J = 2.5, 8.3 Hz, 2 H), 7.35 (t, J = 7.9 Hz, 1 H), 4.06–3.98 (m, 4 H), 3.20 (d, J = 21.6 Hz, 2 H), 2.53 (s, 3 H), 1.22 (t, J = 7.1 Hz, 6 H). |
| 123 | H | Me | H | H | 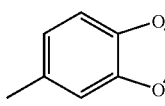 | 8.83 (s, 1 H), 8.13 (s, 1 H), 7.69 (t, J = 8.7 Hz, 3 H), 7.60 (dd, J = 2.1, 8.3 Hz, 1 H), 7.36 (dd, J = 2.1, 8.3 Hz, 2 H), 7.23 (d, J = 1.7 Hz, 1 H), 7.14 (dd, J = 1.7, 7.9 Hz, 1 H), 6.84 (d, J = 8.3 Hz, 1 H), 6.02 (s, 2 H), 4.06–3.96 (m, 4 H), 3.19 (d, J = 22.0 Hz, 2 H), 2.52 (s, 3 H), 1.23 (t, J = 7.1 Hz, 6 H). |
| 124 | H | Me | H | H | 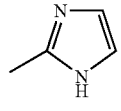 | 10.47 (br, 1 H), 9.18 (s, 1 H), 8.13 (s, 1 H), 7.68 (d, J = 8.3 Hz, 1 H), 7.61–7.58 (m, 3 H), 7.34 (dd, J = 2.5, 8.3 Hz, 2 H), 7.29 (brs, 1 H), 7.12 (brs, 1 H), 4.08–4.01 (m, 4 H), 3.19 (d, J = 22.0 Hz, 2 H), 2.52 (s, 3 H), 1.26 (t, J = 7.1 Hz, 6 H). |
| 125 | H | Me | H | H | 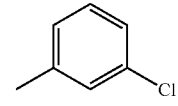 | 8.96 (s, 1 H), 7.71–7.60 (m, 5 H), 7.56 (d, 7.5 Hz, 1 H), 7.46–7.44 (m, 1 H), 7.38–7.33 (m, 3 H), 7.28–7.27 (m, 1 H), 4.06–3.96 (m, 4 H), 3.19 (d, J = 22.0 Hz, 2 H), 2.92 (s, 3 H), 1.22 (t, J = 7.1 Hz, 6 H). |

TABLE 26

| Ex. | R₁ | R₂ | R₃ | R₄ | R₅ | ¹H-NMR(δ:ppm) [CDCl₃] |
|---|---|---|---|---|---|---|
| 126 | Me | H | H | H | 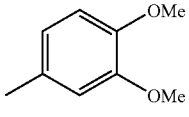 | 8.74 (s, 1 H), 7.71 (d, J = 7.9 Hz, 2 H), 7.66–7.59 (m, 2 H), 7.36–7.33 (m, 3 H), 7.28–7.23 (m, 1 H), 7.23 (dd, J = 1.7, 8.3 Hz, 1 H), 6.88 (d, J = 8.3 Hz, 2 H), 4.04–3.94 (m, 4 H), 3.93 (s, 3 H), 3.85 (s, 3 H), 3.16 (d, J = 22.0 Hz, 2H), 2.93 (s, 3 H), 1.20 (t, J = 7.1 Hz, 6 H). |
| 127 | Me | H | H | H | 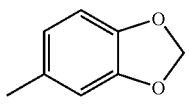 | 8.73 (s, 1 H), 7.68 (d, J = 7.9 Hz, 2H), 7.63–7.59 (m, 2 H), 7.35 (dd, J = 2.5, 8.3 Hz, 2 H), 7.26–7.25 (m, 2 H), 7.15 (dd, J = 1.7, 8.3 Hz, 1 H), 6.84 (d, J = 8.3 Hz, 1 H), 6.02 (s, 2 H), 4.05–3.96 (m, 4 H), 3.18 (d, J = 22.0 Hz, 2 H), 2.92 (s, 3 H), 1.22 (t, J = 7.1 Hz, 6 H). |
| 128 | Me | H | H | H | 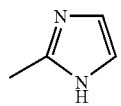 | 10.69 (br, 1 H), 9.03 (s, 1 H), 7.62 (d, J = 4.6 Hz, 2 H), 7.59 (d, J = 7.9 Hz, 2 H), 7.33 (dd, J = 2.5, 8.3 Hz, 2 H), 7.28–7.26 (m, 2 H), 7.11 (brs, 1 H), 4.09–4.00 (m, 4 H), 3.21 (d, J = 22.0 Hz, 2 H), 2.90 (s, 3 H), 1.26 (t, J = 7.1 Hz, 6 H). |

TABLE 26-continued

| Ex. | $R_1$ | $R_2$ | $R_3$ | $R_4$ | $R_5$ | $^1$H-NMR($\delta$:ppm) [CDCl$_3$] |
|---|---|---|---|---|---|---|
| 129 | Me | H | F | H | 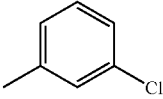 | 9.05 (s, 1 H), 8.36 (dd, J = 6.2, 8.7 Hz, 1 H), 7.69–7.67 (m, 3 H), 7.55 (d, J = 7.5 Hz, 1H), 7.48–7.43 (m, 2 H), 7.40–7.34 (m, 3 H), 7.27–7.22 (m, 1 H), 4.07–3.98 (m, 4 H), 3.21 (d, J = 22.0 Hz, 2 H), 1.23 (t, J = 7.1 Hz, 6 H). |
| 130 | Me | H | F | H | 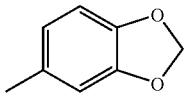 | 8.81 (s, 1 H), 8.35 (dd, J = 6.2, 8.3 Hz, 1 H), 7.68 (d, J = 7.9 Hz, 2 H), 7.44 (dd, J = 2.5, 10.0 Hz, 1 H), 7.38 (dd, J = 2.5, 8.3 Hz, 2 H), 7.25–7.21 (m, 2 H), 7.15 (dd, J = 1.7, 7.9 Hz, 1 H), 6.85 (d, J = 7.9 Hz, 1 H), 6.02 (s, 2 H), 4.06–3.97 (m, 4 H), 3.20 (d, J = 21.6 Hz, 2 H), 1.23 (t, J = 7.1 Hz, 6 H). |

TABLE 27

| Ex. | $R_1$ | $R_2$ | $R_3$ | $R_4$ | $R_5$ | $^1$H-NMR($\delta$:ppm) [CDCl$_3$] |
|---|---|---|---|---|---|---|
| 131 | H | H | F | H | 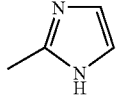 | 10.78 (br, 1H), 9.14 (s, 1 H), 8.34 (dd, J = 6.2, 8.7 Hz, 1 H), 7.61 (d, J = 7.5 Hz, 2H), 7.43 (dd, J = 2.5, 9.6 Hz, 1 H), 7.36 (dd, J = 2.5, 8.3 Hz, 2 H), 7.30 (brs, 1 H), 7.26–7.21 (m, 1 H), 7.12 (brs, 1 H), 4.10–4.01 (m, 4 H), 3.20 (d, J = 21.6 Hz, 2 H), 1.27 (t, J = 7.1 Hz, 6 H). |
| 132 | H | H | H | Me | 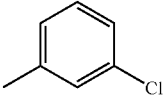 | 9.11 (s, 1 H), 8.19 (d, J = 7.5 Hz, 1 H), 7.74 (d, J = 7.9 Hz, 2 H), 7.70 (t, J = 1.7 Hz, 1 H), 7.64 (d, J = 7.1 Hz, 1 H), 7.57 (d, J = 7.9 Hz, 1 H), 7.45 (ddd, J = 1.2, 2.1, 7.9 Hz, 1 H), 7.43–7.34 (m, 4 H), 4.07–4.00 (m, 4H), 3.21 (d, J = 22.0 Hz, 2 H), 2.68 (s, 3 H), 1.24 (t, J = 7.1 Hz, 6 H). |
| 133 | H | H | H | Me | 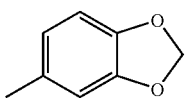 | 8.87 (s, 1 H), 8.19 (d, J = 8.3 Hz, 1H), 7.75 (d, J = 7.5 Hz, 2 H), 7.63 (d, J = 7.5 Hz, 1 H), 7.40 (t, J = 7.5 Hz, 1 H), 7.37 (dd, J = 2.5, 8.3 Hz, 2 H), 7.26 (d, J = 1.7 Hz, 1 H), 7.15 (dd, J = 1.7, 7.9 Hz, 1 H), 6.83 (d, J = 7.9 Hz, 1 H), 6.02 (s, 2 H), 4.07–3.98 (m, 4 H), 3.20 (d, J = 22.0 Hz, 2 H), 2.67 (s, 3 H), 1.24 (t, J = 7.1 Hz, 6 H). |
| 134 | H | H | H | Me | 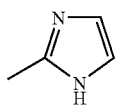 | 10.81 (br, 1 H), 9.15 (s, 1 H), 8.17 (d, J = 7.9 Hz, 1 H), 7.65 (d, J = 7.5 Hz, 2 H), 7.61 (d, J = 7.9 Hz, 1 H), 7.38 (t, J = 7.9 Hz, 1 H), 7.33 (dd, J = 2.5, 8.3 Hz, 2 H), 7.28 (brs, 1 H), 7.12 (brs, 1 H), 4.09–4.01 (m, 4 H), 3.19 (d, J = 22.0 Hz, 2 H), 2.64 (s, 3 H), 1.27 (t, J = 7.1 Hz, 6 H). |
| 135 | H | H | H | Cl | 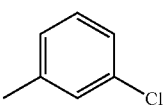 | 9.04 (s, 1 H), 8.26 (dd, J = 1.7, 7.9 Hz, 1 H), 7.87 (dd, J = 1.7, 7.9 Hz, 1 H), 7.77 (s, J = 7.9 Hz, 2 H), 7.71 (t, J = 1.7 Hz, 1 H), 7.57 (d, J = 7.9 Hz, 1 H), 7.49–7.34 (m, 5 H), 4.07–4.00 (m, 4 H), 3.21 (d, J = 22.0 Hz, 2 H), 1.24 (t, J = 7.1 Hz, 6 H). |

TABLE 28

| Ex. | R₁ | R₂ | R₃ | R₄ | R₅ | $^1$H-NMR($\delta$:ppm) [CDCl$_3$] |
|---|---|---|---|---|---|---|
| 136 | H | H | H | Cl | benzo[1,3]dioxol-5-yl | 8.80 (s, 1 H), 8.27 (dd, J = 1.2, 7.9 Hz, 1 H), 7.87 (dd, J = 1.2, 7.9 Hz, 1 H), 7.79 (d, J = 7.9 Hz, 2 H), 7.42 (t, J = 7.9 Hz, 1 H), 7.37 (dd, J = 2.5, 8.3 Hz, 2 H), 7.26 (d, J = 1.7 Hz, 1 H), 7.16 (dd, J = 1.7, 7.9 Hz, 1 H), 6.86 (d, J = 7.9 Hz, 1 H), 6.03 (s, 2 H), 4.06–3.98 (m, 4 H), 3.20 (d, J = 22.0 Hz, 2 H), 1.24 (t, J = 7.1 Hz, 6 H). |
| 137 | H | H | H | Cl | 2-methyl-1H-imidazol-4-yl | 10.08 (br, 1 H), 9.15 (s, 1 H), 8.24 (dd, J = 1.7, 7.9 Hz, 1 H), 7.86 (dd, J =1.7, 7.9 Hz, 1 H), 7.68 (d, J = 7.5 Hz, 2 H), 7.42 (t, J = 7.9 Hz, 1 H), 7.35 (dd, J = 2.5, 8.3 Hz, 2 H), 7.31 (brs, 1 H), 7.14 (brs, 1 H), 4.10–4.03 (m, 4 H), 3.22 (d, J = 21.6 Hz, 2 H), 1.28 (t, J = 7.1 Hz, 6 H). |
| 138 | H | H | H | MeO | benzo[1,3]dioxol-5-yl | 8.38 (s, 1 H), 7.92 (dd, J = 0.8, 7.9 Hz, 1 H), 7.69 (d, J = 7.9 Hz, 2H), 7.45 (t, J = 7.9 Hz, 1 H), 7.34 (dd, J = 2.5, 8.3 Hz, 2 H), 7.23–7.21 (m, 2 H), 7.14 (dd, J = 1.2, 7.9 Hz, 1H), 6.84 (d, J = 7.9 Hz, 1 H), 6.02 (s, 2 H), 4.06–3.96 (m, 7 H), 3.18 (d, J = 22.0 Hz, 2 H), 1.24 (t, J = 7.1 Hz, 6 H). |
| 139 | H | MeO | H | H | benzo[1,3]dioxol-5-yl | 8.83 (s, 1 H), 7.73 (d, J = 8.7 Hz, 1 H), 7.70 (d, J = 2.9 Hz, 1 H), 7.67 (d, J = 8.3 Hz, 2 H), 7.40–7.35 (m, 3H), 7.24 (d, J = 1.7 Hz, 1 H), 7.14 (dd, J = 1.7, 7.9 Hz, 1 H), 6.85 (d, J = 7.9 Hz, 1 H), 6.02 (s, 2 H), 4.06–3.97 (m, 4 H), 3.95 (s, 3 H), 3.19 (d, J = 22.0 Hz, 2H), 1.23 (t, J = 7.1 Hz, 6 H). |
| 140 | H | MeO | H | H | 2-methyl-1H-imidazol-4-yl | 10.97 (br, 1 H), 9.20 (s, 1 H), 7.72–7.70 (m, 2 H), 7.60 (d, J = 7.9 Hz, 2 H), 7.38 (dd, J = 2.9, 9.1 Hz, 1 H), 7.35 (dd, J = 2.5, 8.3 Hz, 2 H), 7.29 (brs, 1 H), 7.12 (brs, 1 H), 4.10–3.98 (m, 4 H), 3.95 (s, 3 H), 3.23 (d, J = 21.6 Hz, 2 H), 1.28 (t, J = 7.1 Hz, 6 H). |

TABLE 29

| Ex. | R₁ | R₂ | R₃ | R₄ | R₅ | $^1$H-NMR($\delta$:ppm) [CDCl$_3$] |
|---|---|---|---|---|---|---|
| 141 | H | Cl | H | Cl | benzo[1,3]dioxol-5-yl | 8.77 (s, 1 H), 8.22 (d, J = 2.5 Hz, 1 H), 7.84 (d, J = 2.5 Hz, 1 H), 7.78 (d, J =7.9 Hz, 2 H), 7.37 (dd, J = 2.5, 8.3 Hz, 2 H), 7.26 (d, J = 1.7 Hz, 1 H), 7.16 (dd, J = 1.7, 7.9 Hz, 1 H), 6.86 (d, J = 7.9 Hz, 1 H), 6.03 (s, 2 H), 4.07–3.98 (m, 4 H), 3.20 (d, J = 22.0 Hz, 2 H), 1.24 (t, J = 7.1 Hz, 6 H). |
| 142 | H | Cl | H | Cl | 2-methyl-1H-imidazol-4-yl | 11.10 (br, 1 H), 9.14 (s, 1 H), 8.22 (d, J = 2.5 Hz, 1 H), 7.84 (d, J = 2.1 Hz, 1 H), 7.68 (d, J = 7.9 Hz, 2 H), 7.36 (dd, J = 2.5, 8.3 Hz, 2 H), 7.29 (brs, 1 H), 7.15 (brs, 1 H), 4.11–4.03 (m, 4 H), 3.20 (d, J = 21.6 Hz, 2 H), 1.29 (t, J = 7.1 Hz, 6 H). |

TABLE 29-continued

| Ex. | R₁ | R₂ | R₃ | R₄ | R₅ | $^1$H-NMR($\delta$:ppm) [CDCl$_3$] |
|---|---|---|---|---|---|---|
| 143 | H | MeO | MeO | H | 3,4-dimethoxyphenyl-methyl | 8.86 (s, 1 H), 7.70 (d, J = 7.9 Hz, 2 H), 7.67 (s, 1 H), 7.36 (dd, J = 2.5, 8.3 Hz, 2 H), 7.30 (d, J = 2.1 Hz, 1 H), 7.22–7.21 (m, 2 H), 6.89 (d, J = 8.3 Hz, 1 H), 4.03–3.95 (m, 10 H), 3.93 (s, 3 H), 3.84 (s, 3 H), 3.17 (d, J = 21.6 Hz, 2 H), 1.21 (t, J =7.1 Hz, 6 H). |
| 144 | H | MeO | MeO | H | benzo[1,3]dioxol-5-ylmethyl | 8.85 (s, 1 H), 7.68–7.66 (m, 3 H), 7.37 (dd, J = 2.1, 8.3 Hz, 2H), 7.23 (d, J = 1.2 Hz, 1H), 7.21 (s, 1 H), 7.14 (dd, J = 1.2, 7.9 Hz, 1 H), 6.85 (d, J = 7.9 Hz, 1 H), 6.02 (s, 2 H), 4.05–3.97 (m, 10 H), 3.20 (d, J = 21.6 Hz, 2 H), 1.23 (t, J = 7.1 Hz, 6 H). |
| 145 | H | MeO | MeO | H | 1H-imidazol-2-yl | 11.25 (br, 1 H), 9.19 (s, 1 H), 7.65 (s, 1H), 7.60 (d, J = 7.9 Hz, 2 H), 7.35 (dd, J = 2.5, 8.3 Hz, 2 H), 7.29 (brs, 1 H), 7.18 (s, 1 H), 7.12 (brs, 1 H), 4.09–4.04 (m, 4 H), 4.03 (s, 3 H), 4.00 (s, 3 H), 3.20 (d, J = 22.0 Hz, 2 H), 1.26 (t, J = 7.1 Hz, 6 H). |

TABLE 30

| Ex. | R₁ | R₂ | R₃ | R₄ | R₅ | $^1$H-NMR($\delta$:ppm) [CDCl$_3$] |
|---|---|---|---|---|---|---|
| 146 | H | Me | H | Me | benzo[1,3]dioxol-5-ylmethyl | 8.85 (s, 1 H), 7.97 (s, 1 H), 7.74 (d, J = 7.9 Hz, 2 H), 7.45 (s, 1 H), 7.35 (dd, J = 2.5, 8.3 Hz, 2 H), 7.26 (d, J = 1.7 Hz, 1 H), 7.15 (dd, J = 1.7, 7.9 Hz, 1 H), 6.84 (d, J = 7.9 Hz, 1 H), 6.02 (s, 2 H), 4.06–3.99 (m, 4 H), 3.20 (d, J = 22.0 Hz, 2 H), 2.63 (s, 3 H), 2.47 (s, 3 H), 1.24 (t, J = 7.1 Hz, 6 H). |
| 147 | H | Me | H | Me | 1H-imidazol-2-yl | 11.01 (br, 1 H), 9.20 (s, 1 H), 7.98 (s, 1 H), 7.64 (d, J = 7.5 Hz, 2 H), 7.46 (s, 1 H), 7.34 (dd, J = 2.5, 8.3 Hz, 2 H), 7.29 (s, 1 H), 7.11 (s, 1 H), 4.13–4.03 (m, 4 H), 3.20 (d, J = 22.0 Hz, 2 H), 2.62 (s, 3 H), 2.47 (s, 3 H), 1.28 (t, J = 7.1 Hz, 6 H). |
| 148 | H | H | Cl | H | 4-bromophenyl-methyl | 9.03 (s, 1H), 8.27 (d, J = 8.3 Hz, 1H), 7.80 (d, J = 2.1 Hz, 1 H), 7.66 (d, J = 7.9 Hz, 2 H), 7.57–7.52 (m, 4 H), 7.48 (dd, J = 2.1, 8.7 Hz, 1 H), 7.38 (dd, J = 2.5, 8.3 Hz, 2 H), 4.09–3.96 (m, 4 H), 3.20 (d, J = 22.0 Hz, 2H), 1.23 (t, J = 7.1 Hz, 6 H). |
| 149 | H | H | Cl | H | 1H-indol-3-yl-methyl | 9.14 (s, 1 H), 8.77 (s, 1 H), 8.29 (d, J = 8.3 Hz, 1 H), 7.89 (d, J = 7.9 Hz, 1 H), 7.82 (d, J = 1.7 Hz, 1 H), 7.78 (d, J = 7.9 Hz, 2 H), 7.47 (dd, J = 2.1, 8.3 Hz, 1 H), 7.39 (d, J = 2.9 Hz, 1 H), 7.35–7.32 (m, 3 H), 7.21 (t, J = 7.5 Hz, 1 H), 7.12 (t, J = 7.5 Hz, 1 H), 3.95–3.85 (m, 4 H), 3.15 (d, J = 22.0 Hz, 2 H), 1.11 (t, J = 7.1 Hz, 6 H). |

TABLE 30-continued

| Ex. | R₁ | R₂ | R₃ | R₄ | R₅ | ¹H-NMR(δ:ppm) [CDCl₃] |
|---|---|---|---|---|---|---|
| 150 | H | H | H | H | 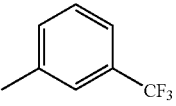 | 9.25 (s, 1 H), 8.36 (d, J = 7.9 Hz, 1 H), 7.94 (s, 1 H), 7.86 (d, J = 7.9 Hz, 1 H), 7.84–7.79 (m, 2 H), 7.74 (d, J = 7.9 Hz, 1 H), 7.69 (d, J = 7.9 Hz, 2 H), 7.58–7.52 (m, 2 H), 7.39 (dd, J = 2.5, 8.3 Hz, 2 H), 4.07–3.98 (m, 4 H), 3.21 (d, J = 22.0 Hz, 2 H), 1.23 (t, J = 7.1 Hz, 6 H). |

TABLE 31

| Ex. | R₁ | R₂ | R₃ | R₄ | R₅ | ¹H-NMR(δ: ppm) [CDCl₃] |
|---|---|---|---|---|---|---|
| 151 | H | H | H | H | 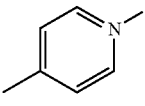 | 9.36(s, 1H), 8.35 (d, J=7.9 Hz, 1H), 8.18(d, J=7.1 Hz, 2H), 7.82 (d, J=4.2 Hz, 2H), 7.64 (d, J=8.3 Hz, 2H), 7.58–7.54(m, 1H), 7.49(d, J=7.1 Hz, 2H), 7.40(dd, J=2.8, 8.3 Hz, 2H), 4.10–4.02(m, 4H), 3.22(d, J=22.0 Hz, 2H), 1.27(t, J =7.1 Hz, 6H). |
| 152 | H | H | H | MeO | 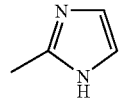 | 11.02(br, 1H), 9.17(s, 1H), 7.93 (dd, J=1.2, 7.9 Hz, 1H), 7.60(d, J=7.9 Hz, 2H), 7.46(t, J=7.9 Hz, 1H), 7.33–7.23(m, 4H), 7.11 (brs, 1H), 4.09–4.01(m, 7H), 3.19 (d, J=21.6 Hz, 2H), 1.28(t, J= 7.1 Hz, 6H). |

Pharmacological Test Example 1

ACAT-1 Inhibitory Action Test 1

Using compounds as shown in Tables 1–31 as test substances, the ACAT-1 inhibitory action of each compound was investigated as follows:

The ACAT-1 enzymatic activity was measured according to the reconstituted vesicle assay (*J. Lipid Res.* 1988, 29, 1683–1692; *Biochem. Biophys. Acta*, 982, 187–195 (1989); *J. Biol. Chem.*, 270, 29532–29540 (1995)).

I. Preparation of Broken Homogenate

SW-13 cells (derived from human adrenal cortical adenocarcinoma) were cultured on a culture plate until confluence in an L-15 culture medium containing 10% fetal bovine serum (FBS) in a carbon dioxide incubator.

Broken homogenates were collected according to a published procedure (hypotonic shock and scrapping method, *Anal. Biochem.*, 116, 298–302 (1981)), subjected to protein quantitation (Bradford method), and stored at −80° C. till use.

II. Preparation of Cholesterol/Phosphatidylcholine (Chol/PC) Vesicle

Chol/PC vesicles (Chol/PC=3.9 mM/12.8 mM) were prepared according to a method described by Chang et al. (Chang, T. Y. et al., *Anal. Biochem.*, 157, 323–330 (1986)).

III. Preparation of 5×DOC/PC

Phosphatidylcholine (50 mg) was dissolved in 5 ml of Buffer A (50 mM Tris-HCl, 5 mM EDTA, 0.05 mM PMSF (phenylmethyl sulfonyl fluoride, Wako Pure Chemical Industries, Ltd., pH: 7.8) containing 50 mg/ml sodium deoxycholate.

IV. Preparation of Enzyme Solution

To 2.6 ml of broken homogenate having a protein concentration of 2.5 mg/ml was added 0.65 ml of 5×DOC/PC, and, after stirring, the mixture was left to stand on ice for 20 minutes. To the mixture was then added 22 ml of the Chol/PC vesicles, and, after stirring, left to stand on ice for another 20 minutes. After centrifugation, suspended matter was removed, thereby giving an enzyme solution.

V. Assay

Each test substance was dissolved in DMSO to a concentration of 1×10⁻³ mol/l.

A 2.5 µl portion of DMSO containing each test substance or DMSO (control), 200 µl of the enzyme solution and 50 µl of a substrate solution (150 mM potassium phosphate buffer (pH: 7.0), 15 mg/ml BSA (FFA free), 2 mM DTT and 0.1 mM [1-¹⁴C] oleoyl coenzyme A (8.0 Ci/mol)) were introduced into screw-cap test tubes and reacted at 37° C. for 30 minutes. The reaction was stopped by adding 4 ml of hexane, 1 ml of 2 M NaCl and 1 ml of [³H]-cholesteryl oleate-containing ethanol (about 10000 dpm). After shaking for 5 minutes, the reaction solution was centrifuged. Into a glass test tube was poured 2 ml of the hexane phase at the top, and another 1 ml of the hexane phase was introduced into a scintillation vial.

With respect to the hexane phase in the glass test tube, the solvent was removed under a nitrogen gas stream. The lipid extract thus obtained was redissolved in a 100 µl of a mixture of chloroform/methanol (2:1), and spotted onto a TLC plate. The TLC plate was developed with hexane/ diethyl ether/acetic acid (73:25:2). Using a bio-imaging analyzer (BAS-2000II, manufactured by Fuji Photo Film Co., Ltd.), the ¹⁴C of the cholesterol ester fraction was quantified.

With respect to the hexane phase in the scintillation vial, ³H was counted after adding a scintillation cocktail. Based on the amount of ³H in the [³H]-cholesteryl oleate-containing ethanol, the extraction efficiency was calculated. Based on the extraction efficiency, the amount of total cholesterol ester produced was calculated. In comparison with the control, decrease in the amount of the total cholesterol ester produced when a test substance was used was expressed as ACAT-1 enzyme inhibition (%).

VI. Results

The results are shown in Tables 32 and 33 below:

TABLE 32

| Example | ACAT-1 enzyme inhibition (%) |
|---|---|
| 1 | 75 |
| 2 | 84 |
| 3 | 71 |
| 4 | 70 |
| 7 | 52 |
| 8 | 60 |
| 18 | 35 |
| 19 | 34 |
| 20 | 72 |
| 21 | 84 |
| 22 | 84 |
| 23 | 59 |
| 24 | 82 |
| 25 | 80 |
| 26 | 69 |
| 27 | 27 |
| 28 | 67 |
| 29 | 64 |
| 30 | 23 |
| 31 | 63 |
| 32 | 58 |
| 33 | 22 |
| 35 | 40 |
| 48 | 27 |
| 49 | 34 |
| 50 | 30 |
| 53 | 49 |
| 54 | 68 |
| 55 | 66 |
| 56 | 64 |

TABLE 33

| Example | ACAT-1 enzyme inhibition (%) |
|---|---|
| 57 | 87 |
| 58 | 67 |
| 60 | 91 |
| 61 | 81 |
| 62 | 78 |
| 64 | 46 |
| 72 | 44 |
| 73 | 47 |
| 77 | 24 |
| 80 | 46 |
| 85 | 79 |
| 87 | 41 |
| 89 | 80 |
| 92 | 73 |
| 93 | 76 |
| 94 | 57 |
| 95 | 30 |
| 103 | 78 |
| 104 | 68 |
| 105 | 61 |
| 106 | 41 |
| 107 | 70 |
| 108 | 83 |
| 109 | 69 |
| 110 | 76 |
| 111 | 69 |
| 112 | 76 |
| 113 | 82 |
| 114 | 67 |
| 115 | 34 |
| 119 | 59 |

VII. Analysis

As is clear from the results shown in Tables 32 and 33, the compounds of the present invention exhibit excellent ACAT-1 inhibitory activity.

Pharmacological Test Example 2

ACAT-1 Inhibitory Action Test 2 (THP-1 Foam Cell Formation Inhibitory Action Test)

The THP-1 foam cell formation inhibitory action (ACAT-1 inhibitory action) of test substances as shown in Tables 1–31 was investigated as described below:

I. Testing Method

THP-1 cells in 10% FBS-RPMI1640 containing 200 nM phorbol 12-myristate 13-acetate (PMA) were seeded in 24-well plates at a density of $7.5 \times 10^5$ cells per well, and incubated for 3 days in a carbon dioxide incubator to differentiate the cells into macrophage-like cells. After the cells were washed with RPMI1640 once, the culture medium was replaced with 1 ml/well RPMI1640 containing 5% lipoprotein deficient serum (LPDS, R. J. Mayer, et al., *J. Biol. Chem.*, 266, 20070 (1991); D. E. Vance, et al., *Biochem. Biophys. Acta*, 792, 39, (1984)), and the cells were further cultured for 8 hours. The culture medium was then replaced with 500 µl of 5% LPDS-RPMI1640 containing acetyl LDL having a protein concentration of 50 µg/ml (AcLDL, Hideki Hakamada et al., "*Doumyakukouka+Koushikessho Kenkyu Strategy*" (Arteriosclerosis Hyperlipidemia Research Strategy); pp 36–41 (1996), Shujunsha Co., Ltd.), 2.5 µl of BSA-[$^{14}$C]oleate complex (J. L. Goldstein, et al., *Method. Enzymol.*, 98, 241 (1983)) and a test substance having a final concentration of $1 \times 10^{-5}$ mol/l. After culturing for 16 hours, the cells were washed once with 0.3% BSA-PBS(−) and twice with PBS(−). To extract the lipid components in the cells, 0.5 ml of hexane/2-propanol (3:2) was added per well, and the cells were left to stand. After 30 minutes, the extract was pooled in a glass test tube. The same extraction procedure was repeated once again, and this extract was combined with the previously obtained extract, and the solvent was then removed under a nitrogen gas stream. The lipid extract thus obtained was redissolved in 100 µl of chloroform/methanol (2:1), and spotted onto a TLC plate. The TLC plate was developed with hexane/diethyl ether/acetic acid (73:25:2). The $^{14}$C of the cholesterol ester fraction was quantified by autoradiography. A bio-imaging analyzer (BAS-2000II, Fuji Film Co., Ltd.) was used for quantification. To each well after lipid extraction was added 0.3 ml of 0.1N NaOH-0.1% SDS, and the cells affixed to the wells were removed and harvested by a rubber policeman. The amount of protein in the cell lysis solution was quantified by a BCA Protein Assay kit (Pierce).

The value obtained by dividing the amount of quantified cholesterol ester (pmol) by the amount of protein (mg) was compared with the value obtained when a test substance was not used, to calculate percent reduction (%). This was referred to as the THP-1 foam cell formation inhibition (%) of each test substance and used as an index for the ACAT-1 activity thereof.

II. Results

Tables 34–37 show the test results.

TABLE 34

| Example | THP-1 foam cell formation inhibition (%) |
|---|---|
| 5 | 93 |
| 6 | 90 |
| 9 | 85 |
| 10 | 88 |
| 11 | 87 |
| 12 | 85 |
| 13 | 88 |
| 14 | 89 |
| 15 | 94 |
| 16 | 94 |
| 17 | 87 |
| 34 | 83 |
| 36 | 88 |
| 37 | 75 |
| 38 | 84 |

TABLE 35

| Example | THP-1 foam cell formation inhibition (%) |
|---|---|
| 39 | 49 |
| 40 | 71 |
| 41 | 92 |
| 42 | 85 |
| 43 | 95 |
| 44 | 73 |
| 45 | 95 |
| 46 | 94 |
| 47 | 85 |
| 51 | 83 |
| 52 | 81 |
| 59 | 93 |
| 63 | 81 |
| 65 | 68 |
| 66 | 76 |
| 67 | 83 |
| 68 | 89 |
| 69 | 45 |
| 70 | 88 |
| 71 | 92 |
| 74 | 37 |
| 75 | 95 |
| 76 | 43 |
| 78 | 93 |
| 79 | 94 |
| 81 | 92 |
| 82 | 87 |
| 83 | 53 |
| 84 | 91 |

TABLE 36

| Example | THP-1 foam cell formation inhibition (%) |
|---|---|
| 86 | 81 |
| 88 | 86 |
| 90 | 88 |
| 91 | 85 |
| 96 | 63 |
| 97 | 84 |
| 98 | 79 |
| 99 | 81 |
| 100 | 49 |
| 101 | 62 |
| 102 | 96 |
| 116 | 42 |
| 117 | 74 |
| 118 | 16 |
| 120 | 81 |
| 121 | 83 |
| 122 | 83 |
| 123 | 83 |
| 124 | 85 |
| 125 | 89 |
| 128 | 96 |
| 129 | 89 |
| 130 | 81 |
| 131 | 90 |
| 126 | 63 |
| 127 | 85 |
| 132 | 77 |
| 133 | 78 |
| 134 | 88 |

TABLE 37

| Example | THP-1 foam cell formation inhibition (%) |
|---|---|
| 135 | 79 |
| 136 | 85 |
| 137 | 80 |
| 138 | 52 |
| 139 | 81 |
| 140 | 77 |
| 141 | 76 |
| 142 | 89 |
| 143 | 36 |
| 144 | 73 |
| 145 | 39 |
| 146 | 72 |
| 147 | 84 |
| 148 | 42 |
| 149 | 37 |
| 150 | 41 |
| 151 | 40 |
| 152 | 38 |

III. Analysis

The results shown in Tables 34–37, as in Tables 32 and 33, establish that the compounds represented by General Formula (1) of the present invention have excellent ACAT-1 inhibitory activity.

Compounds having ACAT-1 inhibitory activity are effective as arteriosclerosis preventive agents and cholesterol absorption inhibitors, as shown in, for example, *The Journal of Biological Chemistry*, Vol.276, No.28, July 14, pp.21324–21330, 2000 and *The Journal of Biological Chemistry*, Vol.275, No.36, September 8, pp.28083–28092, 2000).

Furthermore, compounds having ACAT-1 inhibitory activity are effective for treating arteriosclerosis and lowering LDL-cholesterol, as shown in, for example, "*Nihon Rinsho*, 59(supplement 3), (2001), pp.675–680.

Formulation Example 1

Preparation of Tablets

Using the compound of the present invention obtained in Example 1 as an active ingredient, tablets (2000 tablets) each containing 300 mg of the active ingredient were prepared according to the following formulation:

| | |
|---|---|
| Compound obtained in Example 1 | 600 g |
| Lactose (Japanese Pharmacopoeia) | 67 g |
| Corn starch (Japanese Pharmacopoeia) | 33 g |

-continued

| | |
|---|---|
| Carboxymethylcellulose calcium (Japanese Pharmacopoeia) | 25 g |
| Methylcellulose (Japanese Pharmacopoeia) | 12 g |
| Magnesium stearate (Japanese Pharmacopoeia) | 3 g |

Using the above formulation, the compound of Example 1, lactose, corn starch and carboxymethylcellulose calcium were thoroughly mixed, and the mixture was granulated using the aqueous methylcellulose solution. The granules were passed through a 24-mesh sieve and mixed with magnesium stearate, and the resulting mixture was pressed into tablets, giving the desired tablets.

Formulation Example 2

Preparation of Capsules

Using the compound of Example 1 as an active ingredient, hard gelatin capsules (2000 capsules) each containing 200 mg of the active ingredient were prepared according to the following formulation.

| | |
|---|---|
| Compound of Example 1 | 400 g |
| Crystalline cellulose (Japanese Pharmacopeia) | 60 g |
| Corn starch (Japanese Pharmacopeia) | 34 g |
| Talc (Japanese Pharmacopeia) | 4 g |
| Magnesium stearate (Japanese Pharmacopeia) | 2 g |

Using the above formulation, each ingredient was finely divided and thoroughly mixed to give a uniform mixture. The desired capsules were then prepared by encapsulating the mixture into gelatin capsules having a size appropriate for oral administration.

We claim:

1. A phosphonic acid diester compound represented by General Formula (1):

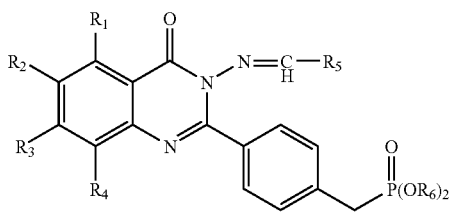

wherein $R_1$, $R_2$, $R_3$ and $R_4$ are the same or different, and represent hydrogen, halogen, lower alkyl or lower alkoxy;

$R_5$ is phenyl having on the phenyl ring 1–3 substituents selected from the group consisting of halogen-substituted lower alkyl, lower alkoxy, halogen-substituted lower alkoxy, phenoxy, benzyloxy, hydroxyl, halogen, nitro, lower alkylthio, di(lower alkyl)amino, lower alkanolyamino, pyrrolidinyl and phenyl, provided that when the substituent is a lower alkoxy group, $R_5$ is substituted with at least one other substituent;
benzodioxolanyl,
naphthyl,
hydroxynaphthyl,
thienyl optionally substituted with one member selected from the group consisting of lower alkyl, halogen and nitro,
furyl optionally substituted with one member selected from the group consisting of lower alkyl, halogen, nitro and halophenyl,
benzofuranyl,
pyrrolyl optionally substituted with one lower alkyl,
imidazolyl optionally substituted with one lower alkyl, or
indolyl, provided that $R_5$ is not mono(lower alkoxy) phenyl; and $R_6$ is lower alkyl.

2. The phosphonic acid diester compound according to claim 1, wherein $R_3$ is halogen.

3. The phosphonic acid diester compound according to claim 1, wherein $R_5$ is thienyl optionally substituted with one member selected from the group consisting of lower alkyl, halogen and nitro.

4. The phosphonic acid diester compound according to claim 1, wherein $R_5$ is furyl optionally substituted with one member selected from the group consisting of lower alkyl, halogen, nitro and halophenyl.

5. The phosphonic acid diester compound according to claim 1, wherein $R_5$ is imidazolyl optionally substituted with one lower alkyl.

6. The phosphonic acid diester compound according to claim 1, wherein $R_5$ is benzodioxolanyl.

7. The phosphonic acid diester compound according to claim 1, wherein $R_1$, $R_2$ and $R_4$ are hydrogen;
$R_3$ is halogen;
$R_5$ is imidazolyl; and
$R_6$ is lower alkyl.

8. The phosphonic acid diester compound according to claim 1, wherein $R_1$, $R_2$ and $R_4$ are hydrogen;
$R_3$ is halogen;
$R_5$ is benzodioxolanyl; and
$R_6$ is lower alkyl.

9. The phosphonic acid diester compound according to claim 1 selected from the group consisting of diethyl (4-{7-chloro-3-[(1 H-imidazol-2-ylmethylene)amino]-4-oxo -3,4-dihydroquinazolin-2-yl}benzylphosphonate and diethyl (4-{3-[(benzo[1,3]dioxol-5-ylmethylene)amino]-7-chloro-4-oxo-3,4-dihydroquinazolin-2-yl}benzylphosphonate.

10. A pharmaceutical composition, which comprises the phosphonic acid diester compound defined in claim 1 and a pharmaceutically acceptable carrier.

11. A method for treating arteriosclerosis in a patient in need of such treatment, which comprises administering to the patient an effective amount of the phosphonic acid diester compound defined in claim 1.

12. A method for lowering the LDL-cholesterol level of a patient in need of such treatment, which comprises administering to the patient an effective amount of the phosphonic acid diester compound defined in claim 1.

13. A method for inhibiting the cholesterol absorption of a patient in need of such treatment, which comprises administering to the patient an effective amount of the patient an effective amount of the phosphonic acid diester compound defined in claim 1.

14. A method for treating Alzheimer's disease in a patient in need of such treatment, which comprises administering to the patient an effective amount of a phosphonic add diester compound represented by General Formula (1):

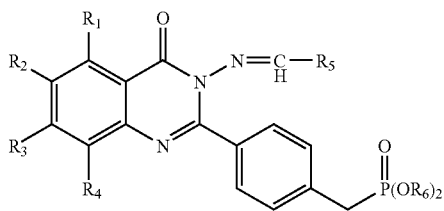

wherein $R_1$, $R_2$, $R_3$ and $R_4$ are the same or different, and represent hydrogen, halogen, lower alkyl or lower alkoxy;

$R_5$ is phenyl having on the phenyl ring 1–3 substituents selected from the group consisting of lower alkyl, halogen-substituted lower alkyl, lower alkoxy, halogen-substituted lower alkoxy, phenoxy, benzyloxy, hydroxyl, halogen, nitro, lower alkylthio, di(lower alkyl)amino, lower alkanolyamino, pyrrolidinyl and phenyl, benzodioxolanyl, naphthyl, hydroxynaphthyl, pyridyl substituted with one lower alkyl, thienyl optionally substituted with one member selected from the group consisting of lower alkyl, halogen and nitro, furyl optionally substituted with one member selected from the group consisting of lower alkyl, halogen, nitro and halophenyl, benzofuranyl, pyrrolyl optionally substituted with one lower alkyl, imidazolyl optionally substituted with one lower alkyl, or indolyl, provided that $R_5$ is not mono(lower alkoxy) phenyl; and $R_6$ is lower alkyl.

* * * * *